United States Patent
Park et al.

(10) Patent No.: US 10,966,686 B2
(45) Date of Patent: Apr. 6, 2021

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Sung-wook Park, Hongcheon-gun (KR); Jin-yong Lee, Hongcheon-gun (KR); Hye-sung Won, Seoul (KR); Mi-young Lee, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 555 days.

(21) Appl. No.: 15/870,475

(22) Filed: Jan. 12, 2018

(65) Prior Publication Data

US 2019/0015077 A1 Jan. 17, 2019

Related U.S. Application Data

(60) Provisional application No. 62/532,645, filed on Jul. 14, 2017.

(30) Foreign Application Priority Data

Aug. 29, 2017 (KR) ........................ 10-2017-0109490

(51) Int. Cl.
*A61B 8/00* (2006.01)
*A61B 8/08* (2006.01)
(Continued)

(52) U.S. Cl.
CPC ................ *A61B 8/488* (2013.01); *A61B 8/06* (2013.01); *A61B 8/4472* (2013.01); *A61B 8/463* (2013.01);
(Continued)

(58) Field of Classification Search
CPC ........... A61B 8/488; A61B 8/463; A61B 8/06; A61B 8/4472; A61B 8/466; A61B 8/5246;
(Continued)

(56) References Cited

U.S. PATENT DOCUMENTS 5,860,927 A 1/1999 Sakaguchi et al.
5,947,903 A 9/1999 Ohtsuki et al.
(Continued)

FOREIGN PATENT DOCUMENTS

CN 103536315 A 1/2014
JP 9-313485 A 12/1997
(Continued)

OTHER PUBLICATIONS

Ginghina et al., "Doppler flow patterns in the evaluation of pulmonary hypertension", Jan. 2009, Romanian Journal of Internal Medicine, vol. 47, Issue 2, 15 pages total, XP 055520711.
(Continued)

*Primary Examiner* — Joel Lamprecht
(74) *Attorney, Agent, or Firm* — Sughrue Mion, PLLC

(57) ABSTRACT

Provided is an ultrasound diagnosis apparatus and a method of operating the ultrasound diagnosis apparatus. The method includes: obtaining first Doppler data of a blood flow introduced into a cardiac ventricle of an object and second Doppler data of a blood flow discharged from the cardiac ventricle; setting a landmark corresponding to a predetermined motion of the cardiac ventricle in each of a first Doppler image generated based on the first Doppler data and a second Doppler image generated based on the second Doppler data; synchronizing the first Doppler image and the second Doppler image based on the set landmark; and displaying the first Doppler image and the second Doppler image that are synchronized.

21 Claims, 16 Drawing Sheets

(51) Int. Cl.
*A61B 8/06* (2006.01)
*G01S 7/52* (2006.01)

(52) U.S. Cl.
CPC ............ *A61B 8/466* (2013.01); *A61B 8/5246* (2013.01); *G01S 7/5205* (2013.01); *G01S 7/52066* (2013.01); *A61B 8/0883* (2013.01); *A61B 8/465* (2013.01); *A61B 8/54* (2013.01); *A61B 8/56* (2013.01)

(58) Field of Classification Search
CPC ......... A61B 8/0883; A61B 8/465; A61B 8/54; A61B 8/56; A61B 8/02; A61B 8/065; A61B 8/4427; A61B 8/467; G01S 7/5205; G01S 7/52066
See application file for complete search history.

(56) References Cited

U.S. PATENT DOCUMENTS

| | | | |
|---|---|---|---|
| 8,303,507 B2 | 11/2012 | Baba et al. | |
| 8,591,417 B2 | 11/2013 | Suzuki et al. | |
| 8,821,401 B2 | 9/2014 | Baba et al. | |
| 9,579,083 B2 | 2/2017 | Guracar | |
| 9,737,282 B2 | 8/2017 | Chen | |
| 2007/0055158 A1* | 3/2007 | Jackson | A61B 8/08 600/443 |
| 2007/0167794 A1* | 7/2007 | Dala-Krishna | A61B 8/06 600/455 |
| 2008/0249414 A1* | 10/2008 | Yang | A61B 8/483 600/445 |
| 2008/0249425 A1 | 10/2008 | Phillips | |
| 2012/0215110 A1* | 8/2012 | Wilkening | G01S 7/5209 600/453 |
| 2014/0107435 A1 | 4/2014 | Sharf et al. | |
| 2014/0125691 A1* | 5/2014 | Lysyansky | A61B 8/488 345/619 |
| 2017/0209125 A1* | 7/2017 | Rai | G06F 3/0488 |

FOREIGN PATENT DOCUMENTS

| | | |
|---|---|---|
| JP | 2001-46372 A | 2/2001 |
| JP | 4189405 B2 | 12/2008 |
| JP | 2010-155073 A | 7/2010 |
| JP | 2014-518129 A | 7/2014 |
| WO | 2006/096915 A1 | 9/2006 |

OTHER PUBLICATIONS

Luxford, et al., "Echocardiography of the tricuspid valve", 2017, Annals of Cardiothoracic Surgery, vol. 6, Issue 3, pp. 223-239, XP 055520700.

Communication dated Nov. 19, 2018, issued by the European Patent Office in counterpart European Patent Application No. 18162375.2.

\* cited by examiner

FIG. 2A
FIG. 2B
FIG. 2C
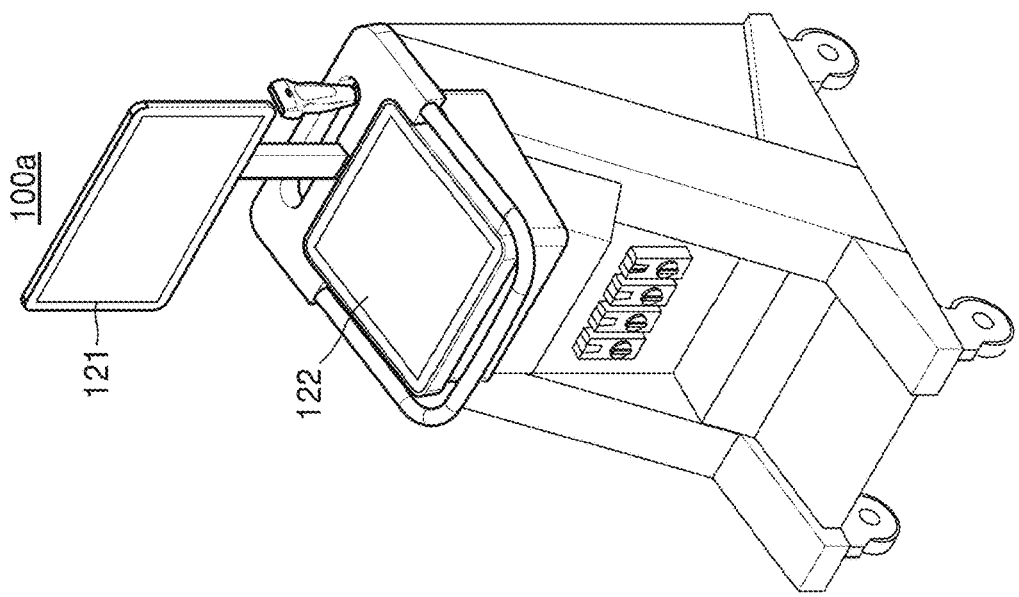
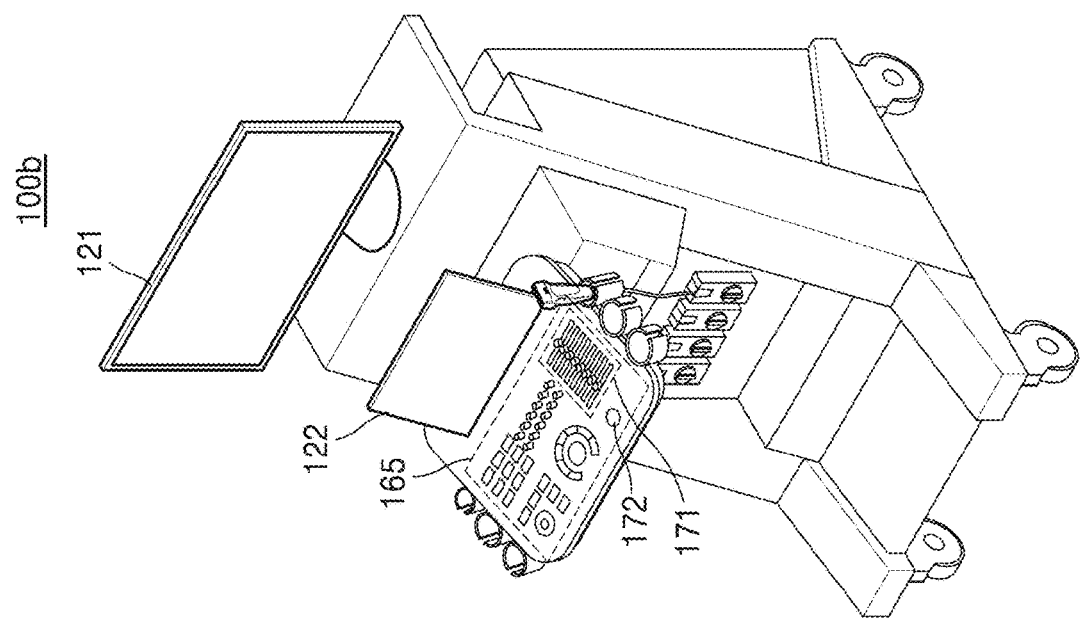
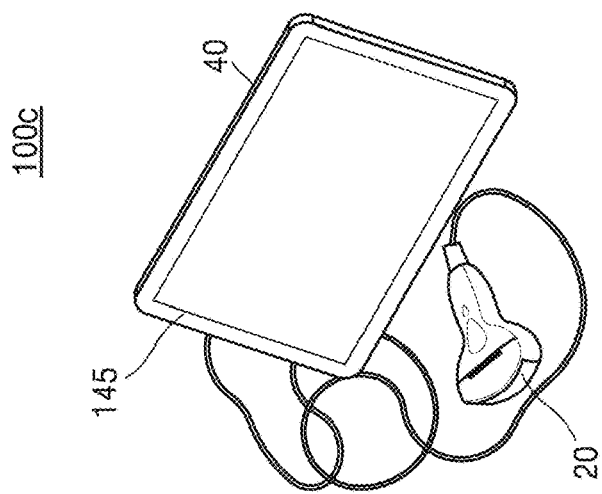

600 image# ULTRASOUND DIAGNOSIS APPARATUS AND METHOD OF OPERATING THE SAME

CROSS-REFERENCE TO RELATED APPLICATIONS

This application claims the benefit of U.S. Provisional Application No. 62/532,645, filed on Jul. 14, 2017, in the US Patent Office and Korean Patent Application No. 10-2017-0109490, filed on Aug. 29, 2017, in the Korean Intellectual Property Office, the disclosures of which are incorporated herein in their entireties by reference.

BACKGROUND

1. Field

The present disclosure relates to ultrasound diagnosis apparatuses and methods of operating the ultrasound diagnosis apparatus.

2. Description of the Related Art

Ultrasound diagnosis apparatuses transmit, to an object, ultrasound signals generated by a transducer of a probe, and receive information of echo signals reflected from the object, thereby obtaining images of an internal part of the object. In particular, an ultrasound diagnosis apparatus is used for medical purposes, e.g., observation of internal organs of an object, detecting abnormalities, assessing injury, etc. Such an ultrasound diagnosis apparatus is safer than other diagnosis apparatuses using X-rays, is capable of displaying images in real-time, and has no risk of radioactive exposure, and thus, the ultrasound diagnosis apparatus is widely used with other image diagnosis apparatuses.

SUMMARY

Provided are ultrasound diagnosis apparatuses capable of synchronizing a first Doppler image generated based on first Doppler data with a second Doppler image generated based on second Doppler data by using a landmark, even when a cycle of heart beat obtained from the first Doppler data of a blood flow introduced into a cardiac ventricle is different from a cycle of heart beat obtained from the second Doppler data of a blood flow discharged from the cardiac ventricle.

The ultrasound diagnosis apparatus may display synchronized first Doppler image and synchronized second Doppler image, and may obtain and display a value of at least one parameter regarding the heart function.

Additional aspects will be set forth in part in the description which follows and, in part, will be apparent from the description, or may be learned by practice of the presented embodiments.

According to an aspect of an embodiment, a method of operating an ultrasound diagnosis apparatus, the method includes obtaining first Doppler data of a blood flow introduced into a cardiac ventricle of an object and second Doppler data of a blood flow discharged from the cardiac ventricle; setting a landmark corresponding to a predetermined motion of the cardiac ventricle in each of a first Doppler image generated based on the first Doppler data and a second Doppler image generated based on the second Doppler data; synchronizing the first Doppler image and the second Doppler image based on the set landmark; and displaying the first Doppler image and the second Doppler image that are synchronized.

Wherein the synchronizing of the first Doppler image and the second Doppler image includes determining a first cycle of a heartbeat of the object based on the first Doppler data and a second cycle of the heartbeat of the object based on the second Doppler data; when the first cycle and the second cycle are different from each other, correcting at least one of the first Doppler image and the second Doppler image to make the first cycle and the second cycle coincide with each other; and synchronizing the first Doppler image and the second Doppler image having the coincided heartbeat cycle due to the correction, based on the landmark.

Wherein the correcting of the at least one of the first and second Doppler images includes correcting a scale in a time axis in a spectrum in the at least one of the first and second Doppler images so that the first cycle and the second cycle coincide with each other; and correcting the Doppler data of the blood flow introduced into or discharged from the cardiac ventricle in the spectrum of the at least one of the first and second Doppler images, according to the correction of the scale in the time axis.

Wherein the correcting of the at least one of the first and second Doppler images includes determining one of the first Doppler image and the second Doppler image as a reference Doppler image; and correcting the other Doppler image not determined as the reference Doppler image based on the determined reference Doppler image, so that the first cycle and the second cycle coincide with each other.

Wherein the cardiac ventricle is the right ventricle, and the predetermined motion of the cardiac ventricle includes one of closing of a pulmonary valve (PV) of the right ventricle, opening of the PV of the right ventricle, closing of a tricuspid valve (TV) of the right ventricle, and opening of the TV of the right ventricle.

Wherein the obtaining of the first Doppler data and the second Doppler data includes obtaining an ultrasound image of the heart of the object; obtaining the first Doppler data of the blood flow introduced into the cardiac ventricle based on a sample volume gate set with respect to a TV of the cardiac ventricle in the ultrasound image; and obtaining the second Doppler data of the blood flow discharged from the cardiac ventricle, based on a sample volume gate set with respect to a PV of the cardiac ventricle in the ultrasound image.

The method further includes obtaining a value of at least one parameter regarding a heart function, based on the first Doppler image and the second Doppler image that are synchronized; and displaying the value of the at least one parameter.

Wherein the at least one parameter comprises at least one of a closure time of a TV, an opening time of a PV, a myocardial performance index (MPI) regarding the heartbeat, an isovolumic relaxation time (IVRT) of the heart, and a isovolumetric contraction time (IVCT) of the heart.

Wherein the displaying of the value of the at least one parameter includes displaying the at least one parameter and the value of the at least one parameter on at least one of the synchronized first Doppler image and the synchronized second Doppler image; and displaying diagnosis information of the heart, based on the value of the at least one parameter.

Wherein the setting of the landmark includes receiving an input of setting a landmark corresponding to the predetermined motion of the cardiac ventricle in each of the first Doppler image and the second Doppler image through a user interface device for controlling operations of the ultrasound diagnosis apparatus.

According to an aspect of another embodiment, an ultrasound diagnosis apparatus includes a probe configured to transmit an ultrasound signal to a heart of an object, and to receive an echo signal reflected from the heart; a processor configured to obtain first Doppler data of a blood flow introduced into a cardiac ventricle and second Doppler data of a blood flow discharged from the cardiac ventricle based on the echo signal, to set a landmark corresponding to a predetermined motion of the cardiac ventricle in each of a first Doppler image generated based on the first Doppler data and a second Doppler image generated based on the second Doppler data, and to synchronize the first Doppler image and the second Doppler image based on the set landmark; and a display configured to display the first Doppler image and the second Doppler image that are synchronized with each other.

Wherein the processor is further configured to determine a first cycle of a heartbeat of the object based on the first Doppler data and a second cycle of the heartbeat of the object based on the second Doppler data, to correct at least one of the first Doppler image and the second Doppler image to make the first cycle and the second cycle coincide with each other when the first cycle and the second cycle are different from each other, and to synchronize the first Doppler image and the second Doppler image having the coincided heartbeat cycle due to the correction, based on the landmark.

Wherein the processor is further configured to correct a scale in a time axis in a spectrum in the at least one of the first and second Doppler images so that the first cycle and the second cycle coincide with each other, and to correct the Doppler data of the blood flow introduced into or discharged from the cardiac ventricle in the spectrum of the at least one of the first and second Doppler images, according to the correction of the scale in the time axis.

Wherein the processor is further configured to determine one of the first Doppler image and the second Doppler image as a reference Doppler image, and to correct the other Doppler image not determined as the reference Doppler image based on the determined reference Doppler image, so that the first cycle and the second cycle coincide with each other.

Wherein the cardiac ventricle is the right ventricle, and the predetermined motion of the cardiac ventricle includes one of closing of a pulmonary valve (PV) of the right ventricle, opening of the PV of the right ventricle, closing of a tricuspid valve (TV) of the right ventricle, and opening of the TV of the right ventricle.

Wherein the processor is further configured to obtain an ultrasound image of the heart of the object based on the echo signal, to obtain the first Doppler data of the blood flow introduced into the cardiac ventricle based on a sample volume gate set with respect to a TV of the cardiac ventricle in the ultrasound image, and to obtain the second Doppler data of the blood flow discharged from the cardiac ventricle, based on a sample volume gate set with respect to a PV of the cardiac ventricle in the ultrasound image.

Wherein the processor is further configured to obtain a value of at least one parameter regarding a heart function, based on the first Doppler image and the second Doppler image that are synchronized, and the display is further configured to display the value of the at least one parameter.

Wherein the at least one parameter comprises at least one of a closure time of a TV, an opening time of a PV, a myocardial performance index (MPI) regarding the heartbeat, an isovolumic relaxation time (IVRT) of the heart, and a isovolumetric contraction time (IVCT) of the heart.

Wherein the display is further configured to display the at least one parameter and the value of the at least one parameter on at least one of the synchronized first Doppler image and the synchronized second Doppler image, and to display diagnosis information of the heart, based on the value of the at least one parameter.

The ultrasound diagnosis apparatus further includes a user interface device configured to control operations of the ultrasound diagnosis apparatus, wherein the user interface device is configured to receive an input for setting a landmark corresponding to the predetermined motion of the cardiac ventricle in the first Doppler image and the second Doppler image.

According to an aspect of another embodiment, a computer-readable recording medium having embodied thereon a program for executing a method of operating an ultrasound diagnosis apparatus, wherein the method includes obtaining first Doppler data of a blood flow introduced into a cardiac ventricle of an object and second Doppler data of a blood flow discharged from the cardiac ventricle; setting a landmark corresponding to a predetermined motion of the cardiac ventricle in each of a first Doppler image generated based on the first Doppler data and a second Doppler image generated based on the second Doppler data; synchronizing the first Doppler image and the second Doppler image based on the set landmark; and displaying the first Doppler image and the second Doppler image that are synchronized.

BRIEF DESCRIPTION OF THE DRAWINGS

These and/or other aspects will become apparent and more readily appreciated from the following description of the embodiments, taken in conjunction with the accompanying drawings in which:

The above and other features and advantages will become more apparent by describing in detail exemplary embodiments thereof with reference to the attached drawings in which reference numerals mean structural elements:

FIGS. 2A to 2C are diagrams of an ultrasound diagnosis apparatus according to an embodiment;

DETAILED DESCRIPTION

Figure 1:
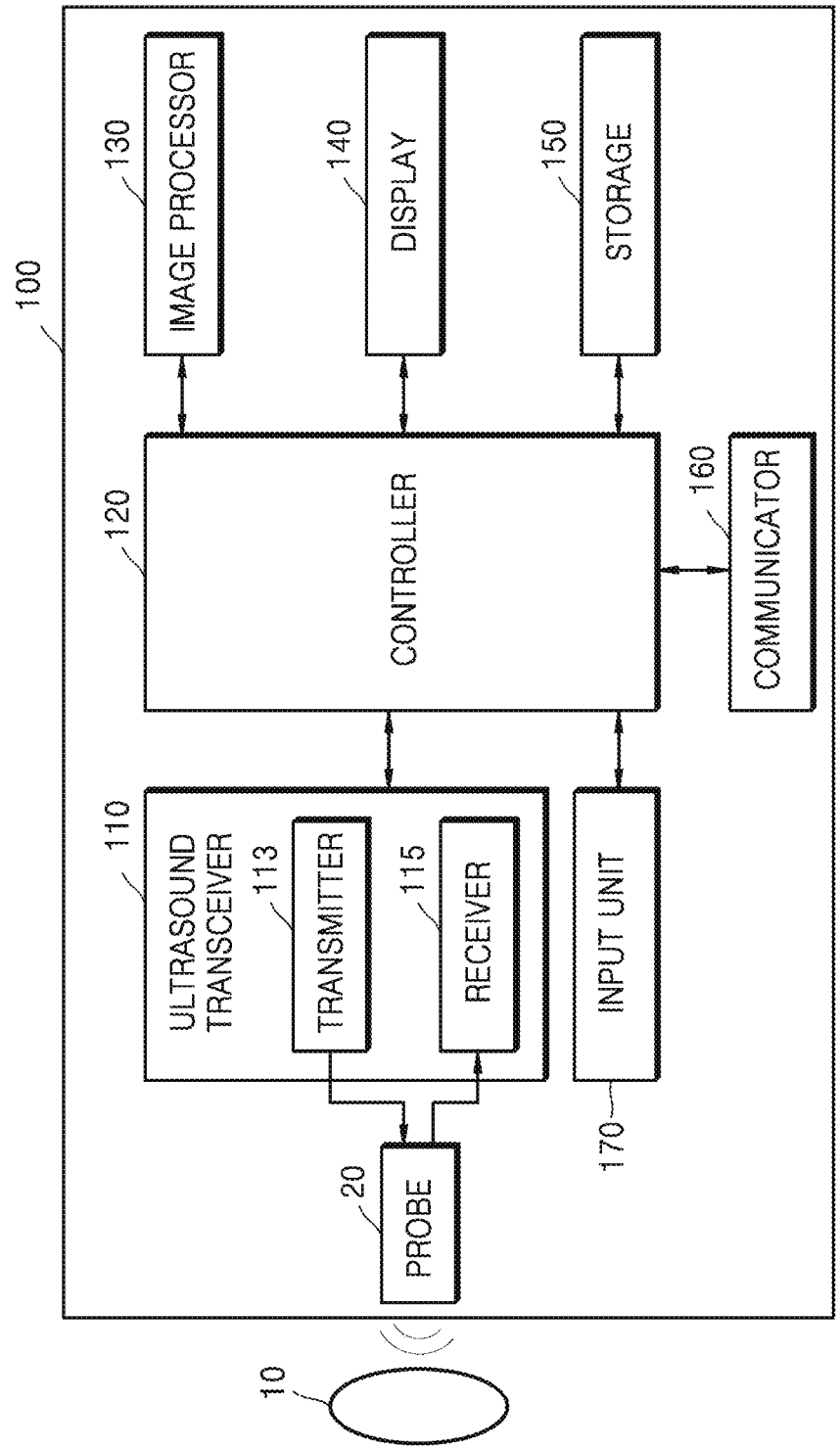
FIG. 1 is a block diagram of an ultrasound diagnosis apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant. In this case, the meaning of the selected terms will be described in the detailed description. Thus, the terms used herein have to be defined based on the meaning of the terms together with the description throughout the specification.

It will be further understood that the terms "comprises" and/or "comprising," when used in this specification, specify the presence of stated components, but do not preclude the presence or addition of one or more components. The term "unit", as used herein, means a software or hardware component, such as a Field Programmable Gate Array (FPGA) or Application Specific Integrated Circuit (ASIC), which performs certain tasks. However, the term "unit" is not limited to software or hardware. A "unit" may advantageously be configured to reside on the addressable storage medium and configured to execute on one or more processors. Thus, a unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and "units" may be combined into fewer components and "units" or may be further separated into additional components and "units".

It will be understood that although the terms "first," "second," etc. may be used herein to describe various components, these components should not be limited by these terms. These components are only used to distinguish one component from another. These components are only used to distinguish one component from another. For example, a second element may be referred to as a first element while not departing from the scope of the present disclosure, and likewise, a first element may also be referred to as a second element. The term and/or includes a combination of a plurality of related described items or any one item among the plurality of related described items.

Throughout the specification, an "image" may denote multi-dimensional data formed of discrete image elements, e.g., pixels in a two-dimensional (2D) image and voxels in a three-dimensional (3D) image.

An "ultrasound image" may denote an image obtained from an object by using an ultrasound signal. An ultrasound image may denote an image obtained by transmitting an ultrasound signal generated by a transducer of a probe to an object, and receiving information of an echo signal reflected from the object. Here, the ultrasound image may vary, for example, may be in any one of an amplitude (A) mode, a brightness (B) mode, a color (C) mode, or a Doppler (D) mode, and the ultrasound image may be a 2D image or a 3D image.

Furthermore, an object may be a human, an animal, or a part of a human or animal. For example, the object may be an organ (e.g., the liver, the heart, the womb, the brain, a breast, or the abdomen), or a blood vessel. Also, the object may include a phantom, and the phantom may denote a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, one or more embodiments of the present disclosure will be described in detail with reference to accompanying drawings to the extent that one of ordinary skill in the art would be able to carry out the present disclosure. However, the present disclosure may be implemented in various manners, and is not limited to one or more embodiments described herein.

Hereinafter, one or more embodiments will be described below with reference to accompanying drawings.

FIG. 1 is a block diagram of an ultrasound diagnosis apparatus 100 according to an embodiment. The ultrasound diagnosis apparatus 100 according to the embodiment may include a probe 20, an ultrasound transceiver 110, a controller 120, an image processor 130, a display 140, a storage 150, a communicator 160, and an input unit 170.

The ultrasound diagnosis apparatus 100 may be implemented as a portable type, as well as a cart type. Examples of a portable ultrasound diagnosis apparatus may include a smart phone including a probe and an application, a laptop computer, a personal digital assistant (PDA), a tablet PC, etc., but are not limited thereto.

The probe 20 may include a plurality of transducers. The plurality of transducers may send an ultrasound signal to an object 10 according to a transmission signal applied from a transmitter 113. The plurality of transducers may receive the ultrasound signal reflected by the object 10 to generate a reception signal. Also, the probe 20 may be implemented as a built-in type in the ultrasound diagnosis apparatus 10, or may be a separation type connected through wires or wirelessly with the ultrasound diagnosis apparatus 100. Also, the ultrasound diagnosis apparatus 100 may include one or a plurality of probes 20 according to an implementation type.

The controller 120 controls the transmitter 113 to generate a transmission signal to be applied to each of the plurality of transducers, taking into account locations of the plurality of transducers included in the probe 20 and a focusing point.

The controller 120 controls a receiver 115 to perform analog-to-digital conversion of the reception signal transmitted from the probe 20 and to generate ultrasound data by adding digital-converted reception signals taking into account the locations of the plurality of transducers and the focusing point.

The image processor 130 generates an ultrasound image by using ultrasound data generated by the receiver 115.

The display 140 may display generated ultrasound image and various information processed by the ultrasound diagnosis apparatus 100. The ultrasound diagnosis apparatus 100 may include one or a plurality of displays 140 according to an implementation type. Also, the display 140 may be implemented as a touch screen by combining with a touch panel.

The controller 120 may control overall operations of the ultrasound diagnosis apparatus 100 and signal flow between internal elements of the ultrasound diagnosis apparatus 100. The controller 120 may include a memory for storing programs for performing functions of the ultrasound diagnosis apparatus 100 or data, and a processor processing the programs or the data. Also, the controller 120 may receive a control signal from the input unit 170 or an external device to control operations of the ultrasound diagnosis apparatus 100.

The ultrasound diagnosis apparatus 100 includes the communicator 160, and may be connected to an external device (e.g., a server, a medical apparatus, and a portable device (smartphone, tablet PC, wearable devices, etc.)) through the communicator 160.

The communicator 160 may include one or more elements allowing communication with the external device, for example, may include at least one of a near field communication module, a wired communication module, and a wireless communication module.

The communicator 160 may receive the control signal and data from the external device and transfer the control signal to the controller 120 so that the controller 120 controls the ultrasound diagnosis apparatus 100 according to the control signal.

Otherwise, the controller 120 may transmit the control signal to the external device via the communicator 160 so as to control the external device according to the control signal of the controller.

For example, the external device may process data thereof according to the control signal of the controller transmitted through the communicator.

The external device may include a program for controlling the ultrasound diagnosis apparatus 100, and thus, the program may include instructions for executing some or all of the operations of the controller 120.

The program may be installed on the external device in advance, or a user of the external device may download the program from a server providing applications and install the program on the external device. The server providing the applications may include a recording medium having the corresponding program thereon.

The storage 150 may store various data or programs for driving and controlling the ultrasound diagnosis apparatus 100, input/output ultrasound data, obtained ultrasound images, etc.

The input unit 170 may receive a user input for controlling the ultrasound diagnosis apparatus 100. For example, the user input may include an input of manipulating a button, a keypad, a mouse, a trackball, a jog switch, a knop, etc., an input of touching a touch pad or a touch screen, a voice input, a motion input, a bio-information input (e.g., iris recognition, fingerprint recognition, etc.), but is not limited thereto.

Examples of the ultrasound diagnosis apparatus 100 according to an embodiment will be described later with reference to FIGS. 2A to 2C.

FIGS. 2A to 2C are diagrams of an ultrasound diagnosis apparatus according to an embodiment.

Referring to FIGS. 2A and 2B, the ultrasound diagnosis apparatuses 100a and 100b may each include a main display 121 and a sub-display 122. One of the main display 121 and the sub-display 122 may be implemented as a touch screen. The main display 121 and the sub-display 122 may display ultrasound images and various information processed by the ultrasound diagnosis apparatuses 100a and 100b. In addition, the main display 121 and the sub-display 122 may be implemented as touch screens providing a graphical user interface (GUI), and thereby receiving data for controlling the ultrasound diagnosis apparatuses 100a and 100b from a user. For example, the main display 121 may display an ultrasound image, and the sub-display 122 may display a control panel as a GUI for controlling the display of the ultrasound image. The sub-display 122 may receive data for controlling the display of the image via the control panel represented as the GUI. The ultrasound diagnosis apparatuses 100a and 100b may control the display of the ultrasound image on the main display 121 by using the received data.

Referring to FIG. 2B, the ultrasound diagnosis apparatus 100b may further include a control panel 165, in addition to the main display 121 and the sub-display 122. The control panel 165 may include a button, a track ball, a jog switch, a knop, etc., and may receive data for controlling the ultrasound diagnosis apparatus 100b from the user. For example, the control panel 165 may include a time gain compensation (TGC) button 171, a freeze button 172, etc. The TGC button 171 is a button for setting a TGC value according to a depth of the ultrasound image. In addition, when sensing an input through the freeze button 172, the ultrasound diagnosis apparatus 100b may maintain a status of displaying a frame image at a corresponding time point.

In addition, the button, the track ball, the jog switch, the knop, etc. included in the control panel 165 may be provided as the GUI on the main display 121 or the sub-display 122.

Referring to FIG. 2C, the ultrasound diagnosis apparatus 100c may be implemented as a portable type. Examples of the ultrasound diagnosis apparatus 100c may include a smart phone including a probe and applications, a laptop computer, a personal digital assistant (PDA), a tablet personal computer (PC), etc., but are not limited thereto.

The ultrasound diagnosis apparatus 100c may include the probe 20 and a main body 40, and the probe 20 may be connected through wire or wirelessly to a side of the main body 40. The main body 40 may include a touch screen 145. The touch screen 145 may display the ultrasound image, various information processed by the ultrasound diagnosis apparatus, and the GUI.

Figure 3:
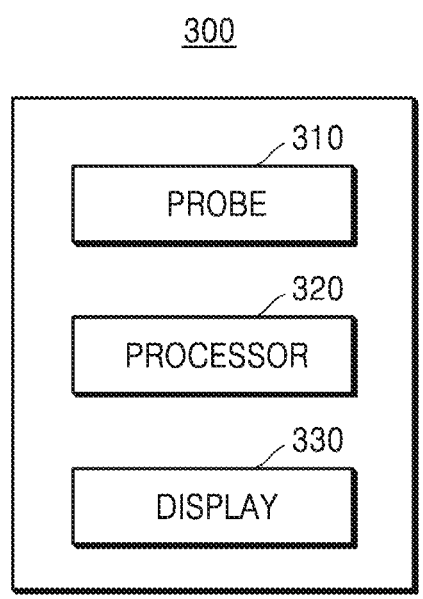
FIG. 3 is a block diagram of an ultrasound diagnosis apparatus according to an embodiment.

FIG. 3 is a block diagram of an ultrasound diagnosis apparatus 300 according to an embodiment.

The ultrasound diagnosis apparatus 300 may include a probe 310, a processor 320, and a display 330. However, not all the elements in FIG. 3 are essential elements. The ultrasound diagnosis apparatus 300 may include more or less elements than the elements shown in FIG. 3. Hereinafter, the elements will be described below.

The probe 310 may include a plurality of transducer devices for converting ultrasound signals and electric signals to each other. That is, the probe 310 may include a transducer array including a plurality of transducer devices, and the plurality of transducer devices may be arranged one-dimensionally or two-dimensionally. Each of the plurality of transducer devices may separately generate an ultrasound signal, and the plurality of transducer devices may simultaneously generate ultrasound signals. The ultrasound signal transmitted from each of the transducer devices is reflected by a discontinuous surface of an impedance in an object. Each transducer device may convert a reflected echo signal into an electric reception signal. The probe 310 transmits an ultrasound signal to the heart of an object, and may receive an echo signal reflected from the heart. Here, the object may be a human being. In detail, the object may include an adult, a child, a fetus, etc.

The processor 320 may obtain first Doppler data of a blood flow introduced into the cardiac ventricle and second Doppler data of a blood flow discharged from the cardiac ventricle, based on the echo signal. In detail, the processor 320 may obtain an ultrasound image of the heart of the object, based on the echo signal. Here, the cardiac ventricle of the heart may correspond to the right ventricle. The processor 320 may obtain the first Doppler data of the blood flow introduced into the right ventricle, based on a sample volume gate set on a tricuspid valve (TV) of the right ventricle in the ultrasound image. Also, the processor 320 may obtain the second Doppler data of the blood flow discharged from the right ventricle, based on a sample volume gate set on a pulmonary valve (PV) of the right ventricle in the ultrasound image.

The processor 320 may obtain a first Doppler image generated based on the first Doppler data and a second Doppler image generated based on the second Doppler data. The processor 320 may set a landmark corresponding to a predetermined motion of the cardiac ventricle, in each of the first Doppler image and the second Doppler image. Here, the cardiac ventricle may correspond to the right ventricle. The predetermined motion may be one of a motion of closing the PV of the right ventricle, a motion of opening PV in the right ventricle, a motion of closing the TV in the right ventricle, and a motion of opening the TV in the right ventricle, but is not limited thereto. For example, the processor 320 may set a landmark corresponding to the motion of closing the PV of the right ventricle, in each of the first Doppler image and the second Doppler image.

The processor 320 may synchronize the first Doppler image and the second Doppler image based on the set landmarks. Here, "synchronization" may denote a process of making a first cycle regarding a cyclic motion of the object obtained from the first Doppler data in the first Doppler image and a second cycle regarding a cyclic motion of the object obtained from the second Doppler data in the second Doppler image equal to each other, and matching times of a predetermined motion of the object. Also, the "synchronization" may include a process of adjusting time intervals so that a predetermined motion of the object may occur at the same time or with a predetermined interval therebetween in the first Doppler image and the second Doppler image.

In detail, the processor 320 may determine a first cycle of the heartbeat of the object based on the first Doppler data and a second cycle of the heartbeat of the object based on the second Doppler data. Here, when the first cycle and the second cycle are equal to each other, the first Doppler image and the second Doppler image may be synchronized with each other based on points of the set landmark.

On the other hand, when the first cycle and the second cycle are different from each other, the processor 320 may correct at least one of the first Doppler image and the second Doppler image so as to coincide the first cycle and the second cycle with each other. The processor 320 may synchronize the first Doppler image and the second Doppler image, the heartbeat cycles of which are coincided with each other through the correction, based on the points of the landmark.

With respect to the method of correcting at least one Doppler image in order to coincide the first cycle and the second cycle, the processor 320 may correct a scale of a time axis in a spectrum of the first Doppler image or the second Doppler image. The processor 320 may correct the Doppler data of the blood flow introduced to or discharged from the cardiac ventricle in the spectrum of the first Doppler image or the second Doppler image, according to the correction on the scale of the time axis.

Also, with respect to the method of correcting the at least one Doppler image in order to coincide the first cycle and the second cycle with each other, the processor 320 may determine one of the first Doppler image and the second Doppler image as a reference Doppler image. The processor 320 may correct the other Doppler image than the reference Doppler image so that the first cycle coincides with the second cycle, based on the determined reference Doppler image.

The processor 320 may obtain a value of at least one parameter regarding the heart function, based on the synchronized first Doppler image and the synchronized second Doppler image. The value of the at least one parameter may be an index used to diagnose the heart function.

Here, the parameter may include at least one of a closure time of TV, an opening time of PV, a myocardial performance index (MPI) regarding the heartbeat, an isovolumic relaxation time (IVRT) of the heart, and an isovolumetric contraction time (IVCT) of the heart, but is not limited thereto.

The display 330 displays a predetermined screen. In detail, the display 330 may display a predetermined screen according to control of the processor 320. The display 330 includes a display panel, and may display an ultrasound image, etc., on the display panel.

The display 330 may display the value of at least one parameter. Also, the display 330 may display at least one parameter and the value of the at least one parameter on at least one of the synchronized first Doppler image and the synchronized second Doppler image.

In addition, the display 330 may display diagnosis information about the heart based on the value of the at least one parameter.

The ultrasound diagnosis apparatus 300 includes a central processor in order to control overall operations of the probe 310, the processor 320, and the display 330. The central processor may be implemented as an array of a plurality of logic gates, or as a combination of a universal microprocessor and a memory storing programs that may be executed in the microprocessor. In addition, one of ordinary skill in the art would appreciate that the central processor may be implemented as other types of hardware.

Figure 4:
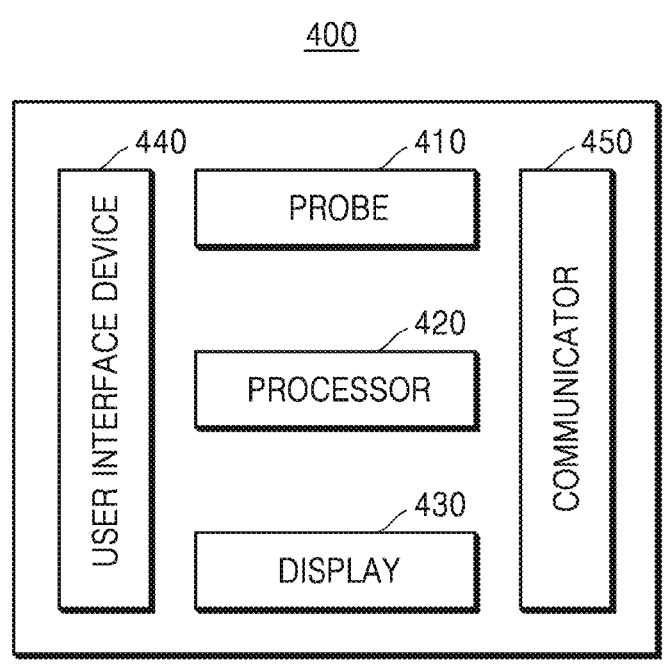
FIG. 4 is a block diagram of an ultrasound diagnosis apparatus according to another embodiment.

FIG. 4 is a block diagram of an ultrasound diagnosis apparatus 400 according to another embodiment.

The ultrasound diagnosis apparatus 400 may include a probe 410, a processor 420, a display 430, a user interface device 440, and a communicator 450.

In FIG. 4, the probe 410, the processor 420, and the display 430 of the ultrasound diagnosis apparatus 400 correspond to the probe 310, the processor 320, and the display 330 of the ultrasound diagnosis apparatus 300 illustrated above with reference to FIG. 3, and thus, detailed descriptions thereof are omitted. The ultrasound diagnosis apparatus 400 may include more or less elements than the elements shown in FIG. 4.

The user interface device 440 is an apparatus for receiving data for controlling the ultrasound diagnosis apparatus 400 from a user. The processor 420 may control the display 430 to generate and output a user interface screen for receiving a predetermined command or data from the user. The display 430 may display an input screen on the display panel for setting a landmark corresponding to a predetermined motion of the cardiac ventricle in each of the first Doppler image and the second Doppler image. Here, the predetermined motion may be one of a motion of closing the PV of the right ventricle, a motion of opening PV in the right ventricle, a motion of closing the TV in the right ventricle, and a motion of opening the TV in the right ventricle.

The user interface device 440 may receive a user input for setting the landmark in each of the first Doppler image and the second Doppler image. The processor 420 sets the landmark in each of the first Doppler image and the second Doppler image based on the user input, and may synchronize the first Doppler image and the second Doppler image with each other based on the set landmark.

The communicator 450 may receive/transmit the data from/to the external device. For example, the communicator 450 may transmit the synchronized first Doppler image and the synchronized second Doppler image to the external device. Also, the communicator 450 may transmit at least one parameter regarding the heart function and a value of the parameter to the external terminal. Here, the external terminal may be a terminal of a patient. Also, the external device may be a server managing diagnosis history of a patient, or a relay server of an application providing a patient with health information. The communicator 450 may be connected to a wireless probe or an external device via a communication network according to WiFi or WiFi direct. In detail, a wireless communication network the communicator 450 may access may include wireless LAN, WiFi, Bluetooth, zigbee, WiFi direct (WFD), ultra wideband (UWB), infrared data association (IrDA), Bluetooth low energy (BLE), and near field communication (NFC), but is not limited thereto.

Also, the ultrasound diagnosis apparatus may further include a memory (not shown). The memory (not shown) may correspond to the memory (not shown) of FIG. 1. The memory (not shown) may store data regarding the ultrasound images (e.g., ultrasound images, ultrasound data, scanning data, Doppler data, Doppler images, diagnosis data of a patient, etc.) and data transmitted to the ultrasound diagnosis apparatus from an external device. The data transmitted from the external device may include information about a patient, data necessary for diagnosing and treating the patient, previous history of the patient, medical work list corresponding to prescription for the patient, etc.

The memory (not shown) may store first Doppler data of a blood flow introduced into the cardiac ventricle and second Doppler data of a blood flow discharged from the cardiac ventricle. Also, the memory (not shown) may store a first Doppler image generated based on the first Doppler data and a second Doppler image generated based on the second Doppler data. Also, the memory (not shown) may store each of the first Doppler image and the second Doppler image, on which the landmark is set respectively. Also, the memory (not shown) may store the first Doppler image and the second Doppler image synchronized based on the landmark. Also, the memory (not shown) may store the value of at least one parameter regarding the heart function, which is obtained based on the synchronized first Doppler image and the second Doppler image.

In addition, the memory (not shown) may store a program executing a method of operating the ultrasound diagnosis apparatus. The memory (not shown) may include codes representing the method of operating the ultrasound diagnosis apparatus. For example, the codes may include a code obtaining the first Doppler data of the blood flow introduced into the cardiac ventricle of the object and the second Doppler data of the blood flow discharged from the cardiac ventricle, a code of setting a landmark corresponding to a predetermined operation of the cardiac ventricle in each of the first Doppler image generated based on the first Doppler data and the second Doppler image generated based on the second Doppler data, a code of synchronizing the first Doppler image and the second Doppler image based on the set landmark, and a code of displaying the synchronized first Doppler image and the synchronized second Doppler image. In addition to the above-described codes, one of ordinary skill in the art would appreciate that other codes for operating the ultrasound diagnosis apparatus may be used.

The ultrasound diagnosis apparatus 400 includes a central processor to control overall operations of the probe 410, the processor 420, the display 430, the user interface device 440, the communicator 450, and the memory (not shown). The central processor may be implemented as an array of a plurality of logic gates, or as a combination of a universal microprocessor and a memory storing programs that may be executed in the microprocessor. In addition, one of ordinary skill in the art would appreciate that the central processor may be implemented as other types of hardware.

Hereinafter, various operations or applications that the ultrasound diagnosis apparatus 300 or 400 performs will be described. Even when the probe 310 or 410, the processor 320 or 420, the display 330 or 430, the user interface 440, the communicator 450, and the memory (not shown) are not specifically described, features that would have been understood or expected by one of ordinary skill in the art may be regarded as their general features. The scope of the present disclosure is not limited to a name or physical/logical structure of a specific component.

Figure 5:
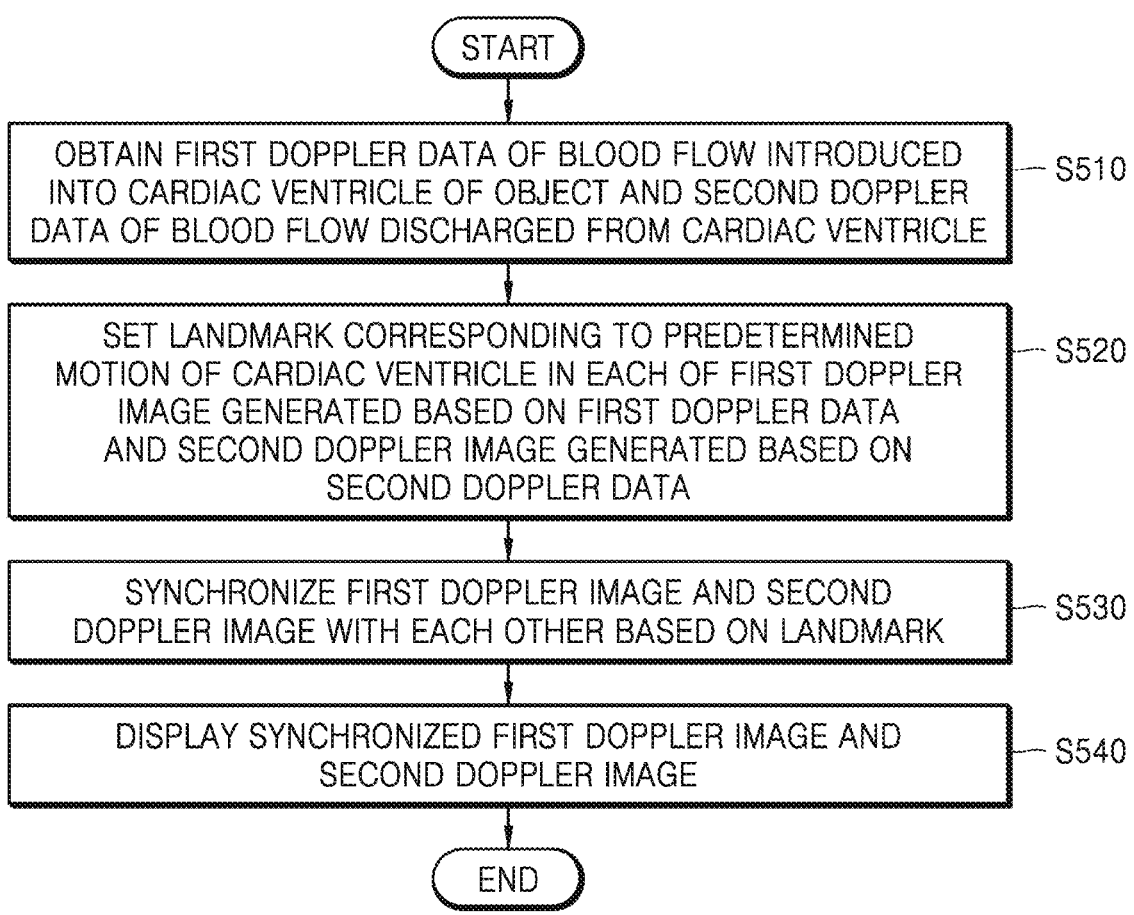
FIG. 5 is a flowchart illustrating a method of operating an ultrasound diagnosis apparatus, according to an embodiment.

FIG. 5 is a flowchart illustrating a method of operating the ultrasound diagnosis apparatus 300, according to an embodiment. Hereinafter, operations of the ultrasound diagnosis apparatus 300 may be applied to the ultrasound diagnosis apparatus 400.

In operation S510 of FIG. 5, the ultrasound diagnosis apparatus 300 may obtain first Doppler data of a blood flow introduced into a cardiac ventricle of an object and second Doppler data of a blood flow discharged from the cardiac ventricle. A method of obtaining the first Doppler data and the second Doppler data will be described in detail later with reference to FIGS. 8 to 10.

In operation S520, the ultrasound diagnosis apparatus 300 may set a landmark corresponding to a predetermined motion of the cardiac ventricle in each of a first Doppler image generated based on the first Doppler data and a second Doppler image generated based on the second Doppler data. Here, the predetermined motion may be one of a motion of closing the PV of the right ventricle, a motion of opening PV in the right ventricle, a motion of closing the TV in the right ventricle, and a motion of opening the TV in the right ventricle, but is not limited thereto.

In detail, the ultrasound diagnosis apparatus 300 may set a landmark corresponding to at least one of closing the PV of the right ventricle, opening the PV of the right ventricle, closing the TV of the right ventricle, and opening the TV of the right ventricle, in each of a first Doppler spectrum in the first Doppler image and a second Doppler spectrum in the second Doppler image. The ultrasound diagnosis apparatus 300 may set a plurality of landmarks respectively corresponding to a plurality of motions of the heart in the first Doppler image and the second Doppler image.

In operation S530, the ultrasound diagnosis apparatus 300 may synchronize the first Doppler image and the second Doppler image based on the landmarks. In detail, the ultrasound diagnosis apparatus 300 may perform an operation of adjusting time intervals so that a predetermined operation of the heart may occur simultaneously or with a predetermined interval in the first Doppler image and the second Doppler image.

For example, the ultrasound diagnosis apparatus 300 may set a point corresponding to a time point when the closing the PV occurs as a landmark, in the first Doppler spectrum of the first Doppler image and the second Doppler spectrum of the second Doppler image. The ultrasound diagnosis apparatus 300 may synchronize the first Doppler image and the second Doppler image based on the landmarks set in the first Doppler image and the second Doppler image, so that the closing the PV may simultaneously occur in the first Doppler spectrum and the second Doppler spectrum.

In operation S540, the ultrasound diagnosis apparatus 300 may display the synchronized first Doppler image and the synchronized second Doppler image.

Figure 6:
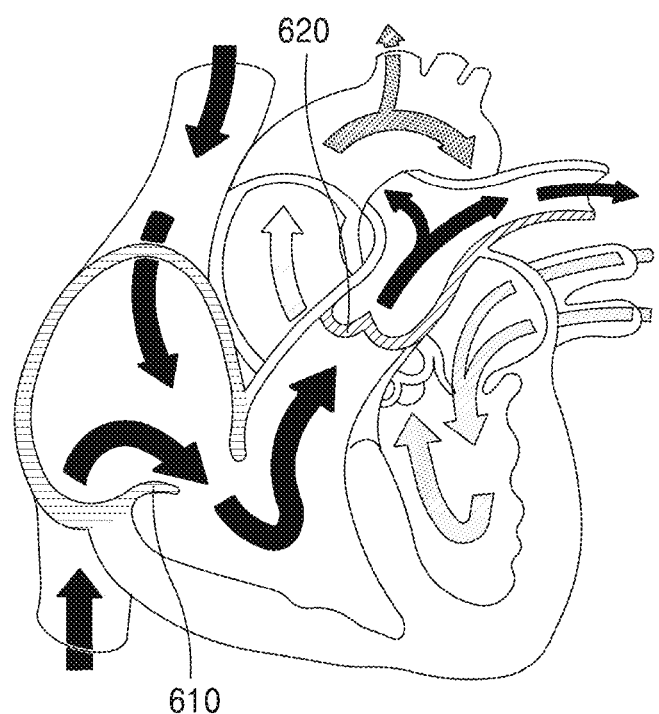
FIG. 6 is a diagram illustrating a structure of the heart of a human being, according to an embodiment.

FIG. 6 is a diagram illustrating a structure of the heart of a human being, according to an embodiment.

Referring to an image 600 of FIG. 6, the heart is an organ that transfers blood to whole body. A blood vessel in which the blood from the heart flows is an artery, and a blood vessel in which the blood flows into the heart is a vein. The blood circulates in an order of the right atrium, the right ventricle, lungs, the left atrium, the left ventricle, whole body, and the right atrium.

As shown in FIG. 6, the heart includes the right ventricle, the right atrium, the left atrium, the left ventricle, the tricuspid valve (TV) 610, the pulmonary valve (PV) 620, and the bicuspid valve. Blood vessels introduced into the heart may include the superior vena cava, the inferior vena cava, and the pulmonary vein. Blood vessels discharged from the heart may include the pulmonary trunk and the aorta.

The TV 610 is a valve existing between the right atrium and the right ventricle, and prevents refluence of the blood from the right atrium to the right ventricle. Diseases related to the TV 610 may include tricuspid stenosis, tricuspid regurgitation, Ebstein's anomaly, tricuspid endocarditis, etc.

The PV 620 is a valve existing between the right ventricle and the pulmonary trunk, and prevents refluence of the blood flowing through the pulmonary trunk. Diseases related to the PV 620 may include pulmonary valve stenosis, pulmonary valvular regurgitation, aortic stenosis, aortic insufficiency, etc.

Figure 7:
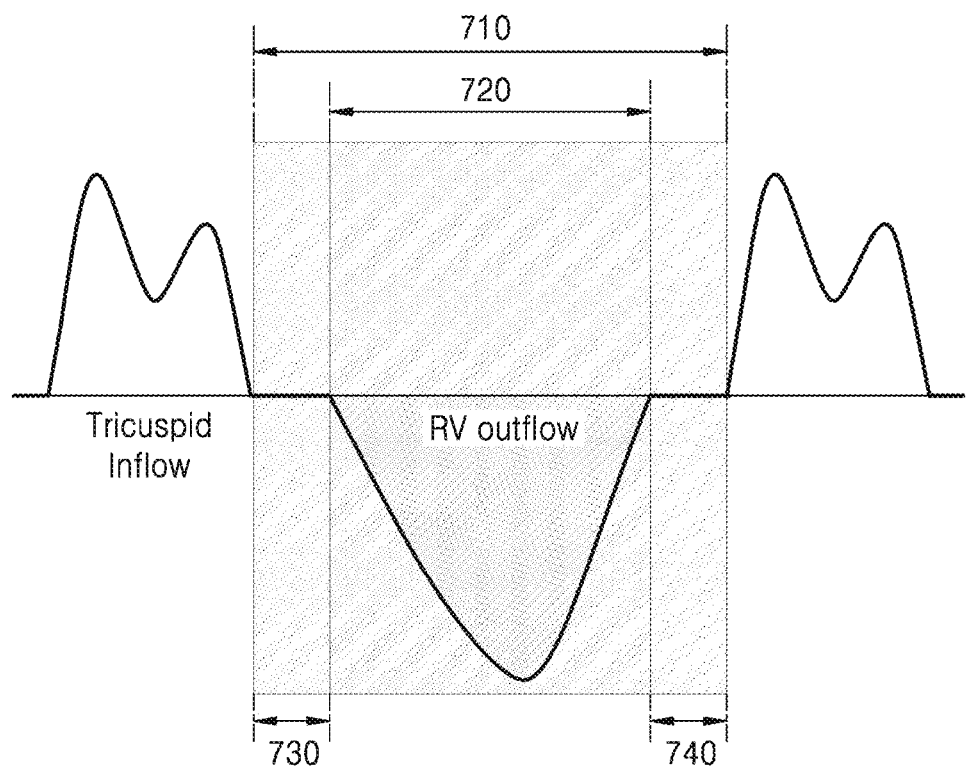
FIG. 7 is a diagram illustrating Doppler data obtained from the heart, according to an embodiment.

FIG. 7 is a diagram illustrating Doppler data obtained from the heart, according to an embodiment.

The ultrasound diagnosis apparatus 300 may generate a first Doppler image after obtaining first Doppler data of the blood flow introduced into the cardiac ventricle. Also, the ultrasound diagnosis apparatus 300 may obtain second Doppler data of the blood flow discharged from the cardiac ventricle to generate a second Doppler image. The ultrasound diagnosis apparatus 300 may obtain a value of at least one parameter regarding the heart function, based on the first Doppler image and the second Doppler image.

As shown in FIG. 7, the parameter may include a closure time of TV of the cardiac ventricle 710, an opening time of PV in the cardiac ventricle 720, an IVCT of the heart 730, an IVRT of the heart 740, and an MPI related to the heart beat, but is not limited thereto.

The IVRT of the heart may be used as an index of diastolic dysfunction of the heart. For example, a range of the IVRT of normal heart may be about 70±12 ms. Also, the IVCT of the heart may be used as an index of systolic dysfunction of the heart.

Also, the MPI may be calculated according to equation 1 below.

$$MPI = \frac{\text{closure time of } TV710 - \text{opening time of semilunar valve 720}}{\text{opening time of semilunar valve 720}} \quad (1)$$

Here, the MPI may be calculated as a ratio of time, and is not affected by a shape of the cardiac ventricle. Therefore, the ultrasound diagnosis apparatus 300 may calculate the MPI by using the spectrum in the Doppler image, and may diagnose functions of the left ventricle and the right ventricle quantitatively. Also, the MPI may be used to quantitatively evaluate the function of the heart of an adult, and a child having congenital heart defect.

In addition, the MPI may be calculated according to equation 2 below.

$$MPI = \frac{IVCT \text{ of the heart } 730 - IVRT \text{ of the heart } 740}{\text{opening time of semilunar valve} 720} \quad (2)$$

The MPI may be calculated according to equation 1 and equation 2 above, and one of ordinary skill in the art would appreciate that the MPI may be calculated according to an equation combining other parameters.

In addition, since the first Doppler data of the blood flow introduced into the TV and the second Doppler data of the blood flow discharged to the PV in different cycles are obtained, the ultrasound diagnosis apparatus 300 may correct at least one of the first Doppler data and the second Doppler data so that the first cycle of the heart obtained from the first Doppler data and the second cycle of the heart obtained from the second Doppler data may coincide with each other. The ultrasound diagnosis apparatus 300 may obtain parameters regarding the heart function, based on the corrected Doppler data.

Figure 8:
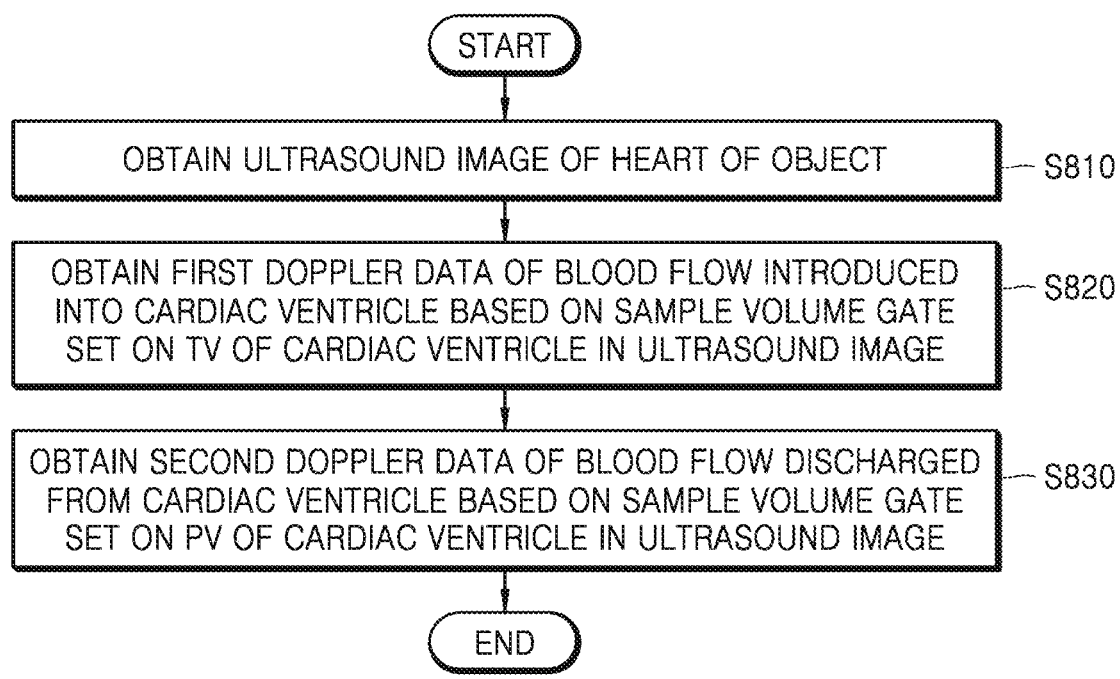
FIG. 8 is a flowchart illustrating a method of obtaining Doppler data from the heart of an object, in an ultrasound diagnosis apparatus, according to an embodiment.

FIG. 8 is a flowchart illustrating a method of obtaining Doppler data from a heart of an object in the ultrasound diagnosis apparatus 300 according to an embodiment;

In operation S810, the ultrasound diagnosis apparatus 300 may obtain an ultrasound image of the heart of an object.

In operation S820, the ultrasound diagnosis apparatus 300 may obtain first Doppler data of a blood flow introduced into the cardiac ventricle, based on a sample volume gate set on the TV of the cardiac ventricle in the ultrasound image.

The ultrasound diagnosis apparatus 300 may obtain the Doppler data of a sample volume located at changed sample volume gate, while changing location of the sample volume gate. The sample volume denotes a restricted region where a Doppler signal is received according to the operation of the sample volume gate.

In detail, the ultrasound diagnosis apparatus 300 may locate the sample volume gate at the TV of the cardiac ventricle, and may obtain the first Doppler data of the blood flow introduced into the cardiac ventricle from the sample volume gate located at the TV.

In operation S830, the ultrasound diagnosis apparatus 300 may obtain the second Doppler data of the blood flow discharged from the cardiac ventricle, based on the sample volume gate set on the PV of the cardiac ventricle in the ultrasound image. In detail, the ultrasound diagnosis apparatus 300 may locate the sample volume gate at the PV of the cardiac ventricle, and may obtain the second Doppler data of the blood flow discharged to the cardiac ventricle from the sample volume gate located at the PV.

Figure 9:
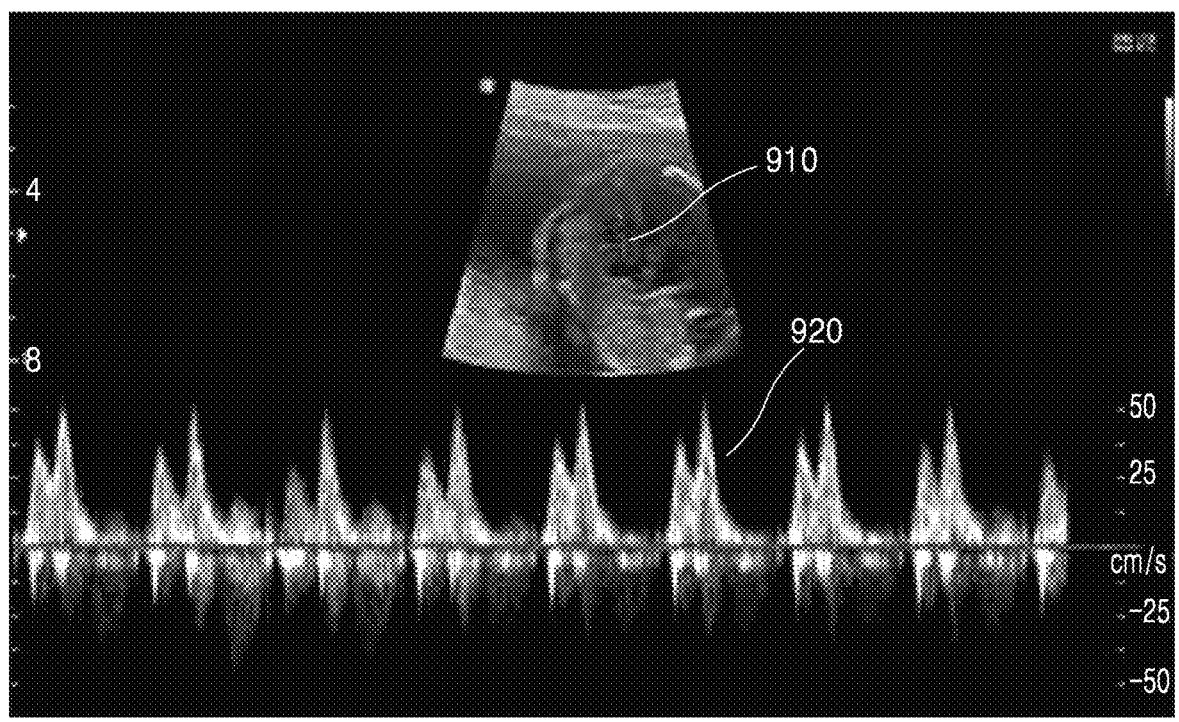
FIGS. 9 and 10 are diagrams illustrating an ultrasound image and a Doppler image provided by an ultrasound diagnosis apparatus, according to an embodiment.
Figure 10:
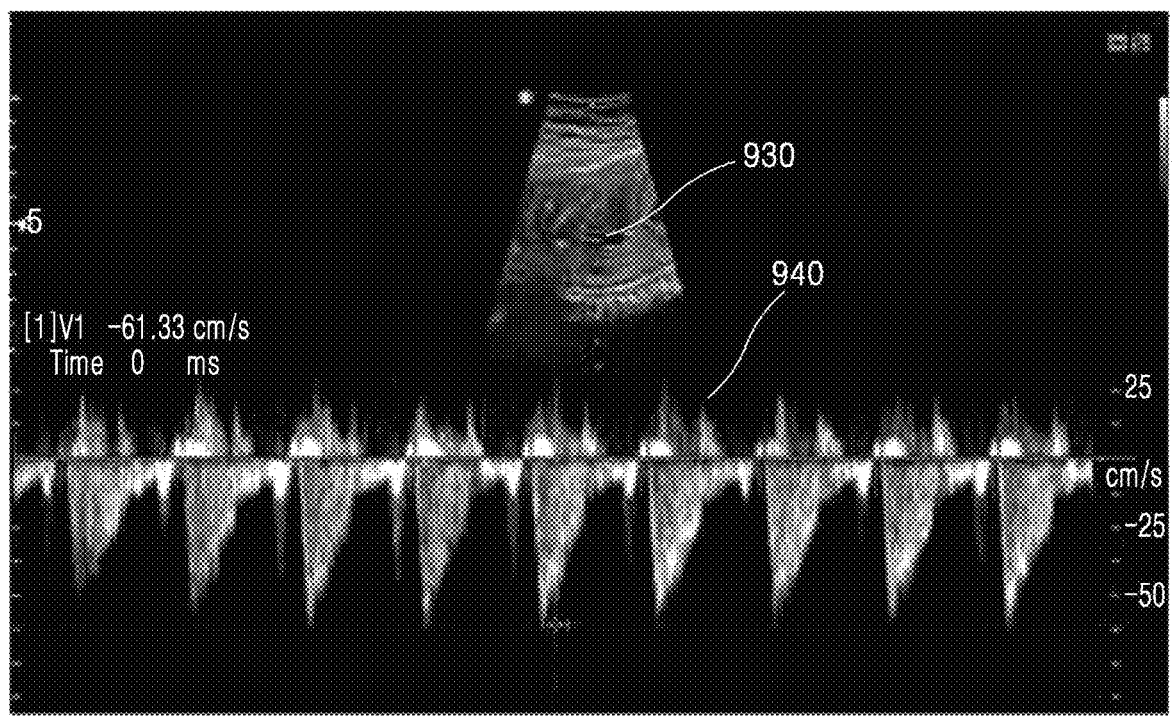

FIGS. 9 and 10 are diagrams illustrating an ultrasound image and a Doppler image provided by the ultrasound diagnosis apparatus 300 according to an embodiment.

As shown in FIG. 9, the ultrasound diagnosis apparatus 300 irradiates an ultrasound signal to the heart of an object by using the probe, and receives an echo signal reflected from the heart to obtain an ultrasound image about the heart. The ultrasound diagnosis apparatus 300 may display the obtained ultrasound image. The ultrasound diagnosis apparatus 300 may locate the sample volume gate at a location 910 corresponding to the TV of the cardiac ventricle in the ultrasound image by using a scan line. The ultrasound diagnosis apparatus 300 may obtain the first Doppler data of the blood flow introduced into the cardiac ventricle from the sample volume gate. The ultrasound diagnosis apparatus 300 may represent the first Doppler data of the blood flow introduced into the cardiac ventricle as a first Doppler spectrum 920.

As shown in FIG. 10, the ultrasound diagnosis apparatus 300 may locate the sample volume gate at a location 930 corresponding to the PV of the cardiac ventricle in the ultrasound image by using the scan line. The ultrasound diagnosis apparatus 300 may obtain the second Doppler data of the blood flow discharged from the cardiac ventricle, from the sample volume gate. The ultrasound diagnosis apparatus 300 may represent the second Doppler data of the blood flow discharged from the cardiac ventricle as a second Doppler spectrum 940.

Figure 11:
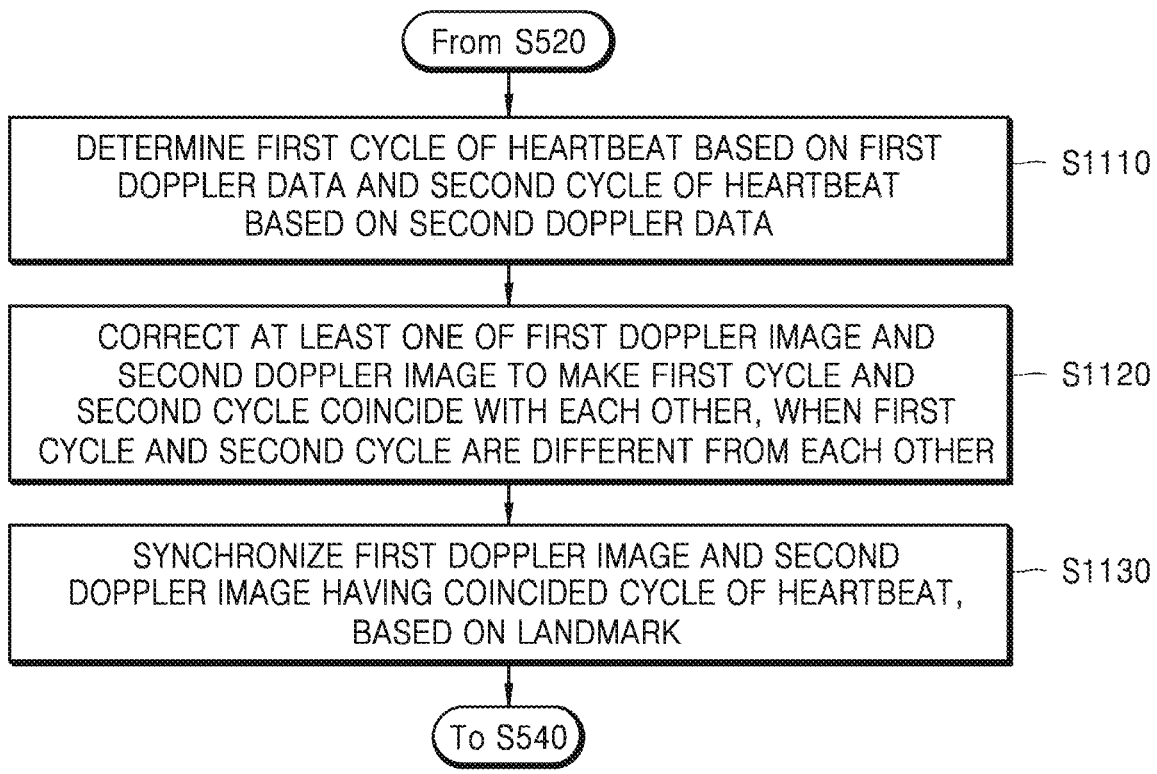
FIG. 11 is a flowchart illustrating a method of synchronizing a first Doppler image and a second Doppler image by using a landmark in an ultrasound diagnosis apparatus, according to an embodiment.

FIG. 11 is a flowchart illustrating a method of synchronizing a first Doppler image and a second Doppler image by using a landmark in the ultrasound diagnosis apparatus 300 according to an embodiment.

In operation S1110, the ultrasound diagnosis apparatus 300 may determine a first cycle of the heartbeat of the object based on the first Doppler data, and may determine a second cycle of the heartbeat of the object based on the second Doppler data.

For example, the first cycle is a cycle of the heart beat with respect to the first Doppler data of the blood flow introduced to the cardiac ventricle, and the second cycle is a cycle of the heart beat with respect to the second Doppler data of the blood flow discharged from the cardiac ventricle.

In operation S1120, when the first cycle and the second cycle are different from each other, the ultrasound diagnosis apparatus 300 may correct at least one of the first Doppler image and the second Doppler image so that the first cycle and the second cycle coincides with each other.

The first cycle determined based on the first Doppler data obtained from the TV according to the systolic and diastolic movements of the heart and the second cycle determined based on the second Doppler data obtained from the PV. The ultrasound diagnosis apparatus 300 may use the first Doppler image generated based on the first Doppler data of the blood flow introduced into the cardiac ventricle and the second Doppler image generated based on the second Doppler data of the blood flow discharged from the cardiac ventricle in order to obtain values of parameters regarding the heart function. When the first cycle and the second cycle are different from each other, an error may occur when the values of first parameters that are obtained respectively from the first Doppler image and the second Doppler image are obtained. Therefore, the ultrasound diagnosis apparatus 300 may correct at least one of the first Doppler image and the second Doppler image so that the first cycle and the second cycle may coincide with each other.

According to an embodiment, the ultrasound diagnosis apparatus 300 may automatically correct a scale of a time axis in the spectrum of the at least one Doppler image so that the first cycle and the second cycle may coincide with each other. The ultrasound diagnosis apparatus 300 may automatically correct the Doppler data of the blood flow introduced into or discharged from the cardiac ventricle, in the spectrum of the at least one Doppler image according to the scale correction in the time axis.

According to another embodiment, the ultrasound diagnosis apparatus 300 may determine at least one of the first Doppler image and the second Doppler image as a reference Doppler image. The ultrasound diagnosis apparatus 300 may correct the other Doppler image than the reference Doppler image based on the reference Doppler image, so that the first cycle and the second cycle may coincide with each other.

In operation S1130, the ultrasound diagnosis apparatus 300 may synchronize the first Doppler image and the second Doppler image, the heartbeat cycles of which are matched to each other through the correction, based on the landmark.

The ultrasound diagnosis apparatus 300 may synchronize the first Doppler image and the second Doppler image with each other so that a predetermined motion of the heart may occur simultaneously in the first and second Doppler images, based on the landmark corresponding to the predetermined motion of the heart set in each of the first Doppler image and the second Doppler image having the coincided heart beat cycles.

Figure 12:
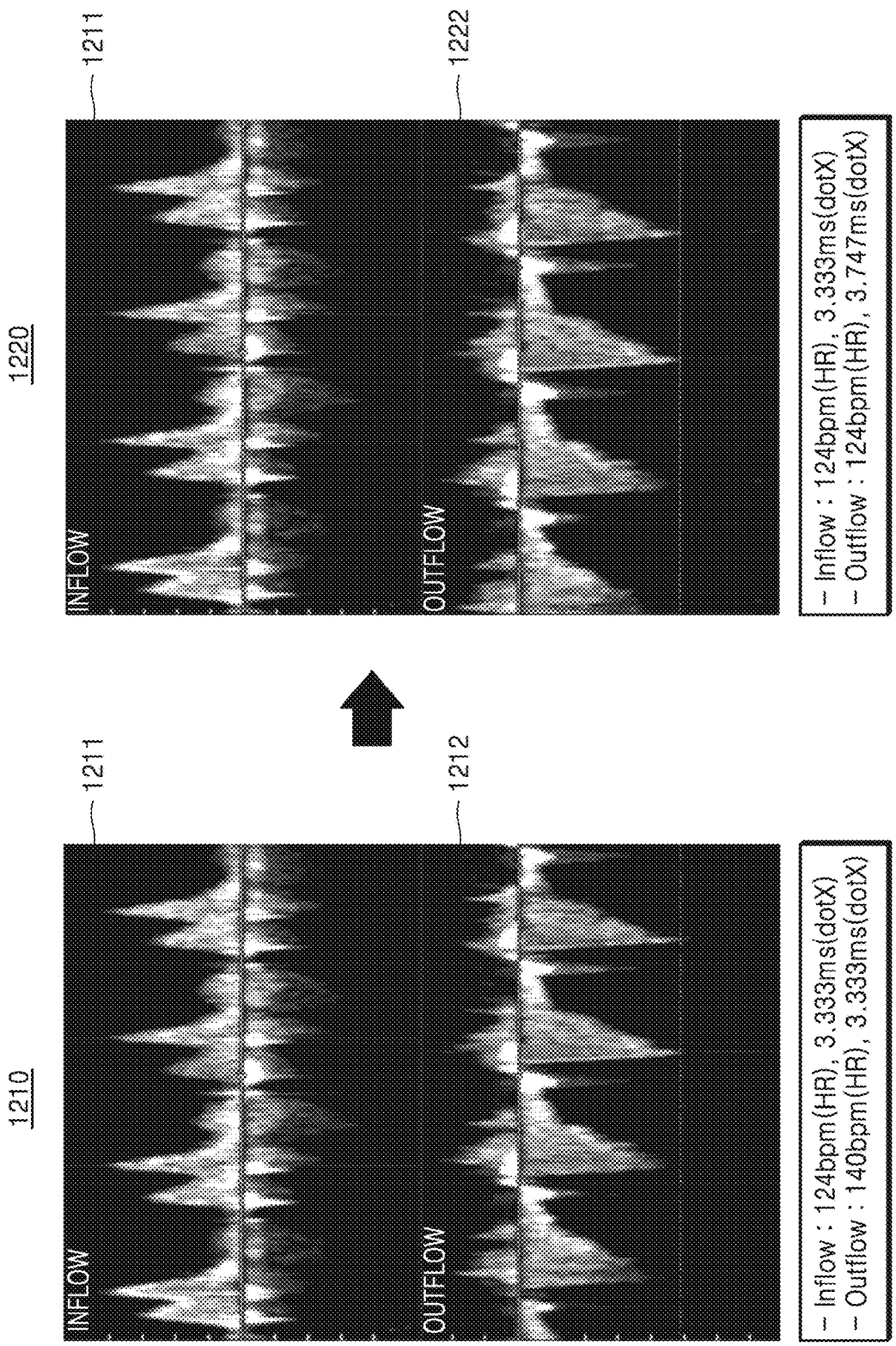
FIG. 12 is a diagram illustrating a method of correcting Doppler images with respect to Doppler data having different cycles, in an ultrasound diagnosis apparatus, according to an embodiment.

FIG. 12 is a diagram illustrating a method of correcting Doppler images with respect to Doppler data having different cycles in the ultrasound diagnosis apparatus 300 according to an embodiment.

The ultrasound diagnosis apparatus 300 may locate a sample volume gate at a point corresponding to the TV of the right ventricle in the ultrasound image, and may obtain the first Doppler data of the blood flow introduced into the cardiac ventricle from the sample volume gate at the point corresponding to the TV.

As shown in FIG. 12, the ultrasound diagnosis apparatus 300 may display a first Doppler spectrum 1211 about the first Doppler data of the blood flow introduced into the right ventricle. Also, the ultrasound diagnosis apparatus 300 may obtain first cycle information about the heart of the object, wherein the first cycle information represents that the heart rate of the object is 124 bpm and one dot represented in the first Doppler spectrum 1211 is 3.333 ms, based on the first Doppler spectrum 1211 of the blood flow introduced into the right ventricle.

Also, the ultrasound diagnosis apparatus 300 may locate a sample volume gate at a point corresponding to the PV of the right ventricle in the ultrasound image, and may obtain the second Doppler data of the blood flow discharged from the cardiac ventricle based on the sample volume gate located at the point corresponding to the PV.

As shown in FIG. 12, the ultrasound diagnosis apparatus 300 may display a second Doppler spectrum 1212 of the second Doppler data of the blood flow discharged from the right ventricle. Also, the ultrasound diagnosis apparatus 300 may obtain second cycle information about the heart of the object, wherein the second cycle information represents that the heart rate of the object is 140 bpm and one dot represented in the second Doppler spectrum 1212 is 3.333 ms, based on the second Doppler spectrum 1212 of the blood flow discharged from the right ventricle.

The ultrasound diagnosis apparatus 300 may display the first Doppler spectrum 1211 and the second Doppler spectrum 1212 together as one Doppler image 1210. Also, the ultrasound diagnosis apparatus 300 may display the first cycle information and the second cycle information respectively on the first Doppler spectrum 1211 and the second Doppler spectrum 1212. In addition, as shown in FIG. 12, the ultrasound diagnosis apparatus 300 may display the first cycle information and the second cycle information on a lower portion of the Doppler image 1210.

Since the first cycle and the second cycle are different from each other, the ultrasound diagnosis apparatus 300 may correct at least one of the first Doppler image and the second Doppler image so that the first cycle and the second cycle coincide with each other.

As shown in FIG. 12, the ultrasound diagnosis apparatus 300 may correct a scale of the time axis in the second Doppler spectrum 1212 in order to coincide the first cycle and the second cycle with each other, and to generate a corrected second Doppler spectrum 1222. In detail, the ultrasound diagnosis apparatus 300 may correct the Doppler data of the blood flow introduced into the cardiac ventricle and/or the Doppler data of the blood flow discharged from the cardiac ventricle in the second Doppler spectrum 1212 according to the scale correction in the time axis, and may generate the corrected second Doppler spectrum 1222.

As a result of correction, the ultrasound diagnosis apparatus 300 may obtain corrected second cycle information about the heart of the object, wherein the corrected second cycle information represents that the heart rate of the object is 124 bpm and one dot in the second Doppler spectrum 1222 is 3.747 ms, based on the corrected second Doppler spectrum 1222.

That is, the ultrasound diagnosis apparatus 300 may correct the second cycle information of the second Doppler spectrum 1212 to coincide with the first cycle information of the first Doppler spectrum 1211. The ultrasound diagnosis apparatus 300 may display the first Doppler spectrum 1211 and the corrected second Doppler spectrum 1222 together as one Doppler image 1220. Also, the ultrasound diagnosis apparatus 300 may display the first cycle information and the corrected second cycle information on a lower portion of the Doppler image 1220.

Figure 13:
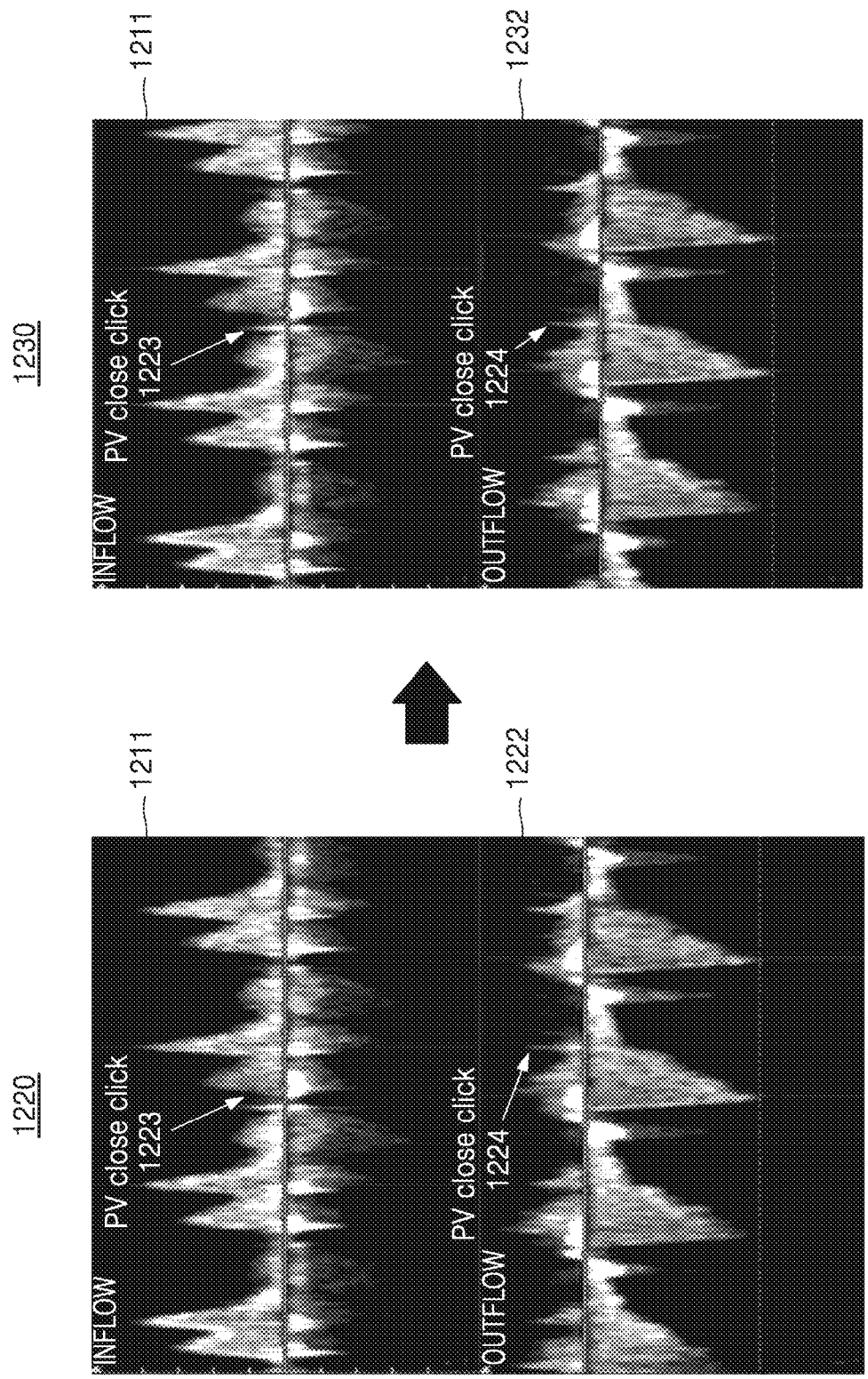
FIG. 13 is a diagram illustrating a method of synchronizing a first Doppler image and a second Doppler image by using a landmark, in an ultrasound diagnosis apparatus, according to an embodiment.

FIG. 13 is a diagram illustrating a method of synchronizing a first Doppler image and a second Doppler image by using a landmark in the ultrasound diagnosis apparatus 300 according to an embodiment.

Referring to the Doppler image 1220 of FIG. 13, the ultrasound diagnosis apparatus 300 may set a point corresponding to an operation of closing the PV of the right ventricle in the first Doppler spectrum 1211 as a first landmark 1223. The ultrasound diagnosis apparatus 300 may set a point corresponding to an operation of closing the PV of the right ventricle in the second Doppler spectrum as a second landmark 1224.

Here, although the point corresponding to the operation of closing the PV of the right ventricle is set as the landmark, one of ordinary skill in the art would appreciate that a point corresponding to opening of the PV of the right ventricle, a point corresponding to closing of the TV of the right ventricle, and a point corresponding to opening of the TV of the right ventricle may be set as a landmark.

Referring to the Doppler image 1230 of FIG. 13, the ultrasound diagnosis apparatus 300 sets the first landmark 1223 in the first Doppler spectrum 1211 and the second landmark 1224 in the second Doppler spectrum 1224 at an equal time point in the time axis, to generate synchronized first Doppler spectrum 1211 and second Doppler spectrum 1232.

Figure 14:
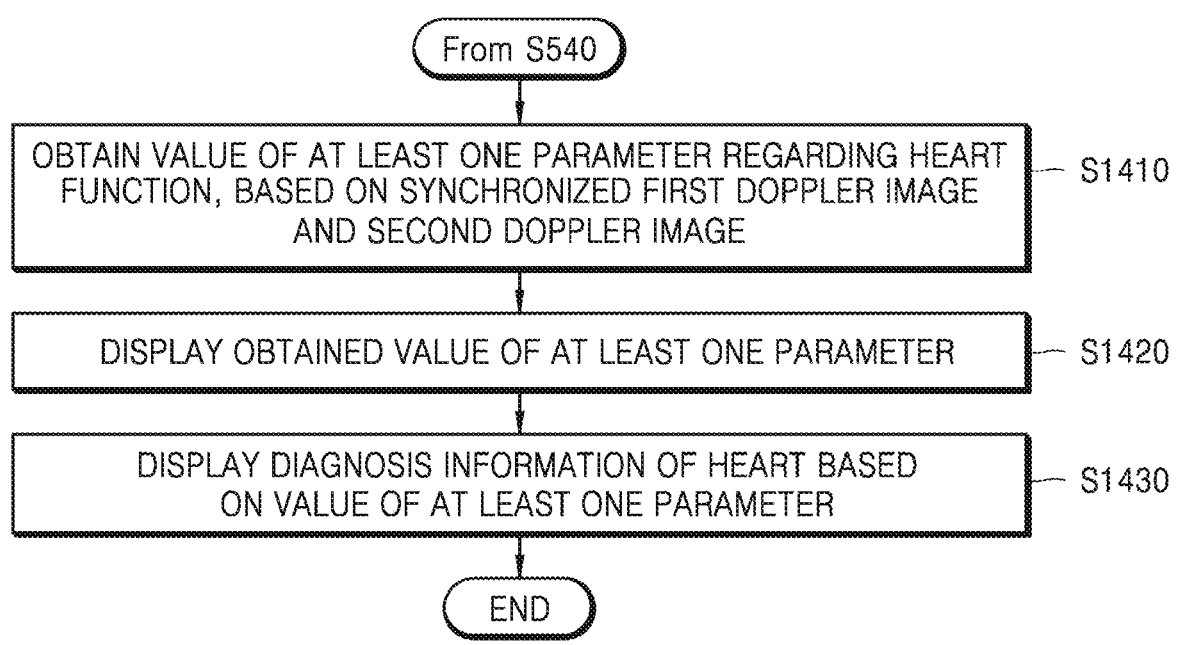
FIG. 14 is a flowchart illustrating a method of representing a parameter regarding heart function and a value of the parameter in a Doppler image, in an ultrasound diagnosis apparatus, according to an embodiment.

FIG. 14 is a flowchart illustrating a method of representing a parameter regarding cardiac function and a value of the parameter in a Doppler image in the ultrasound diagnosis apparatus 300, according to an embodiment.

In operation S1410, the ultrasound diagnosis apparatus 300 may obtain a value of at least one parameter regarding the heart function, based on the synchronized first Doppler image and the synchronized second Doppler image. Here, the at least one parameter may include at least one of a closure time of TV, an opening time of PV, an MPI regarding the heartbeat, an IVRT of the heart, and an IVCT of the heart.

In operation S1420, the ultrasound diagnosis apparatus 300 may display the obtained value of the at least one parameter. The ultrasound diagnosis apparatus 300 may display the at least one parameter and the value of the at least one parameter on at least one of the synchronized first Doppler image and the synchronized second Doppler image.

In operation S1430, the ultrasound diagnosis apparatus 300 may display diagnosis information of the heart, based on the value of the at least one parameter.

Figure 15:
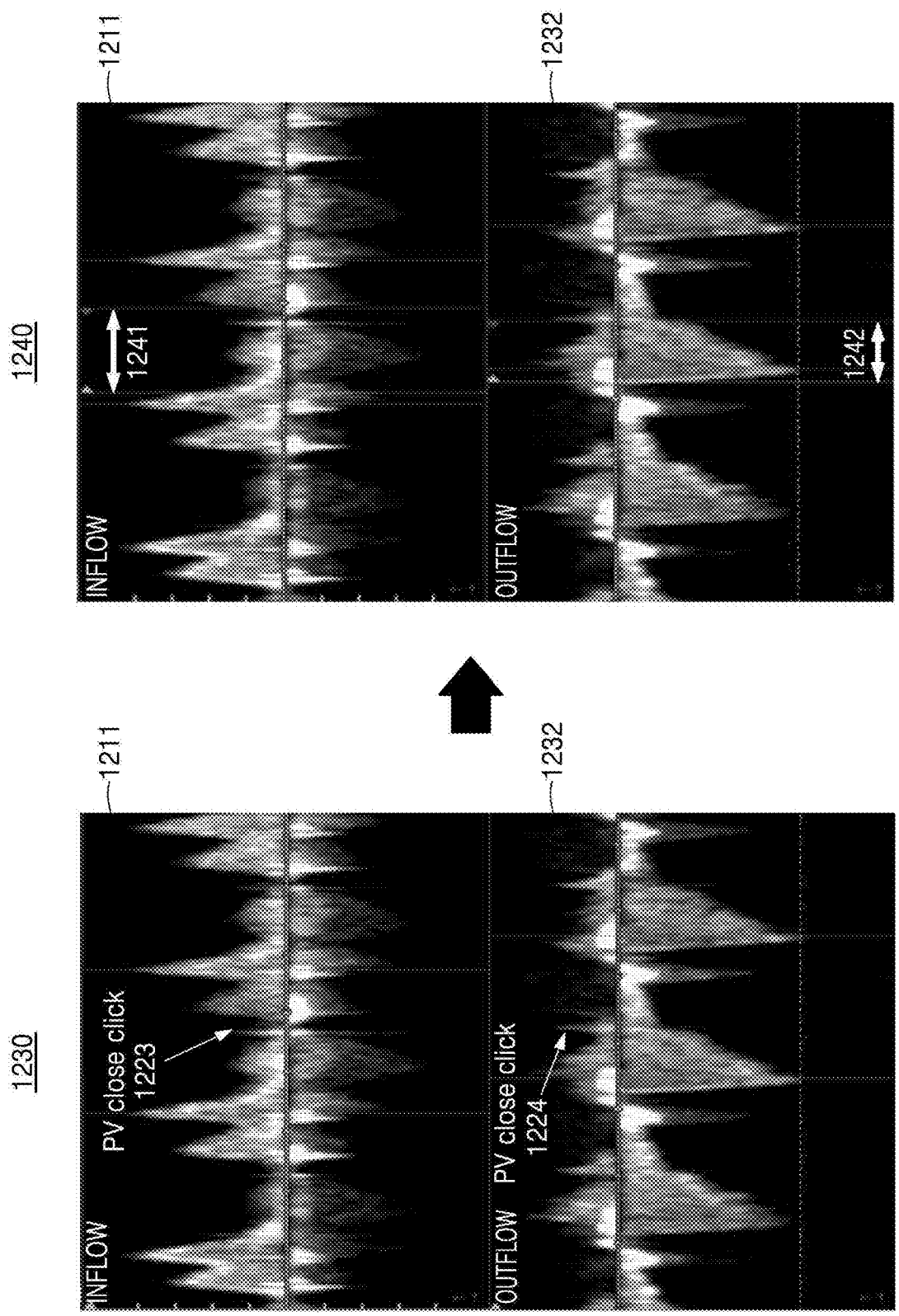
FIG. 15 is a diagram of a Doppler image representing a parameter regarding heart function and a value of the parameter, in an ultrasound diagnosis apparatus, according to an embodiment.

FIG. 15 is a diagram of a Doppler image representing a parameter regarding the heart function and a value of the parameter in the ultrasound diagnosis apparatus 300 according to an embodiment.

Referring to the Doppler image 1230 of FIG. 15, the ultrasound diagnosis apparatus 300 sets the first landmark 1223 in the first Doppler spectrum 1211 and the second landmark 1224 in the second Doppler spectrum 1224 at an equal time point in the time axis, to generate synchronized first Doppler spectrum 1211 and second Doppler spectrum 1232.

Referring to a Doppler image 1240 of FIG. 15, the ultrasound diagnosis apparatus 300 may calculate the closure time 1241 of the TV, based on the first Doppler spectrum 1211. Also, the ultrasound diagnosis apparatus 300 may calculate the opening time 1242 of the PV, based on the second Doppler spectrum 1232. The ultrasound diagnosis apparatus 300 may express sections corresponding to the closure time 1241 of the TV and the opening time 1242 of the PV in each of the Doppler spectrums, and may display the closure time 1241 of the TV and the opening time 1242 of the PV.

Also, the ultrasound diagnosis apparatus 300 may calculate the IVRT and the IVCT of the heart, based on the first Doppler spectrum 1211 and the second Doppler spectrum 1232.

Figure 16:
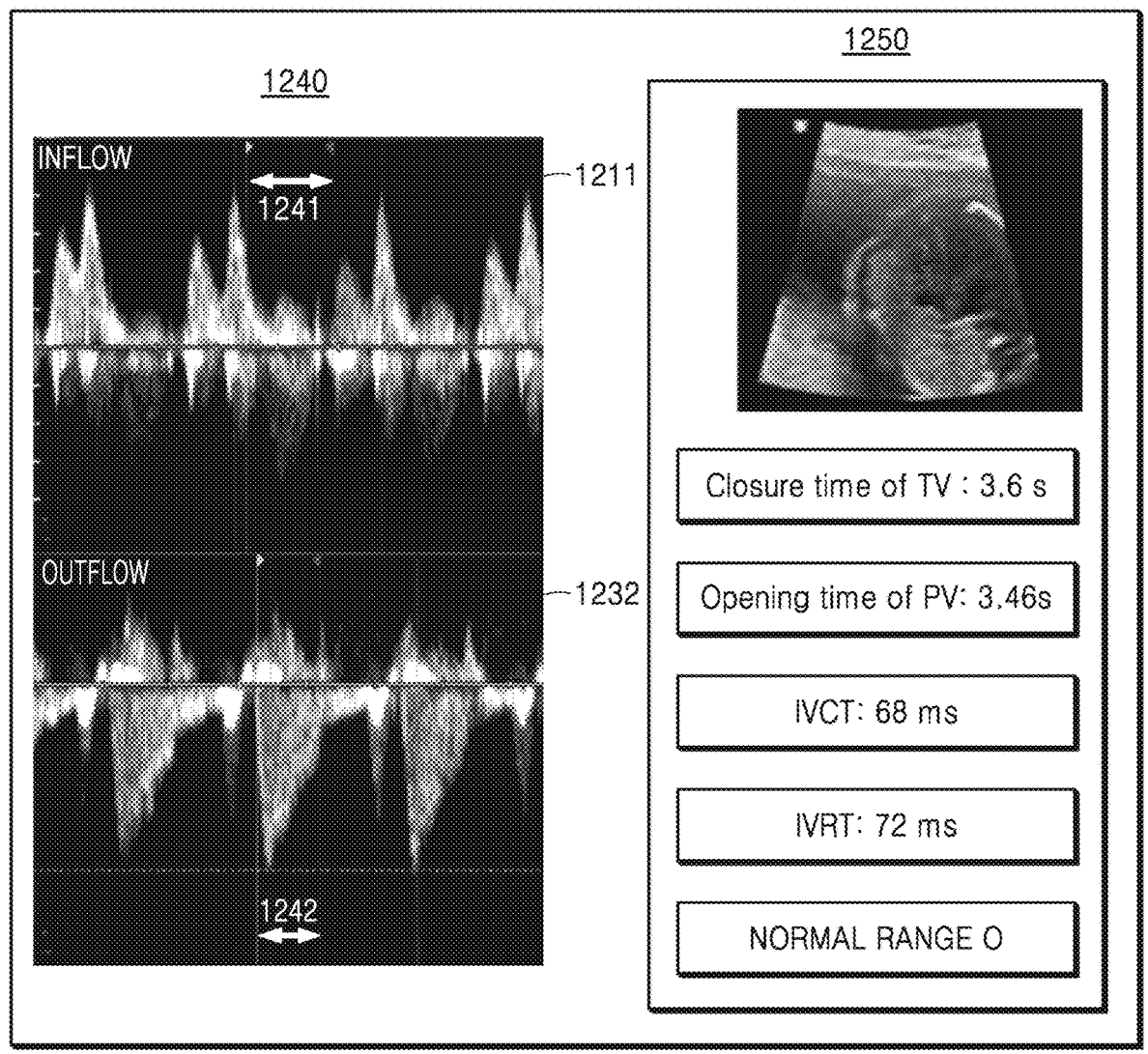
FIG. 16 is a diagram of a Doppler image representing a parameter regarding heart function and a value of the parameter, in an ultrasound diagnosis apparatus, according to another embodiment.

FIG. 16 is a diagram of a Doppler image representing a parameter regarding cardiac function and a value of the parameter in the ultrasound diagnosis apparatus 300 according to another embodiment.

As shown in FIG. 16, the ultrasound diagnosis apparatus 300 may synchronize the first Doppler spectrum 1211 of the blood flow introduced into the right ventricle and the second Doppler spectrum 1232 of the blood flow discharged from the right ventricle, and may display the first Doppler spectrum 1211 and the second Doppler spectrum 1232 as one Doppler image 1240. The ultrasound diagnosis apparatus 300 may determine the parameters regarding the heart function, and may obtain the values of the parameters based on the Doppler image 1240. Also, the ultrasound diagnosis apparatus 300 may express indexes and sections used to obtain the parameters on the Doppler image 1240.

Here, the parameters may include at least one of a closure time of TV, an opening time of PV, an IVCT, an IVRT, and MPI regarding the heartbeat, but are not limited thereto. Also, the MPI may be calculated by combining values of a plurality of parameters.

Referring to an image 1250 of FIG. 16, the ultrasound diagnosis apparatus 300 may display an ultrasound image, and may display parameters used to diagnose the heart function and values of the parameters, e.g., closure time of TV: 3.6 s, opening time of PV: 3.46 s, IVCT: 68 ms, IVRT: 72 ms.

Also, the ultrasound diagnosis apparatus 300 may display the diagnosis information representing the diagnosis result of the heart of the object, based on the parameters used to diagnose the heart function and the values of the parameters. For example, as shown in the image 1250 of FIG. 16, the ultrasound diagnosis apparatus 300 may display the information that the heart of the object is in normal state, based on the information representing "closure time of TV: 3.6 s, opening time of PV: 3.46 s, IVCT: 68 ms, IVRT: 72 ms". Also, the diagnosis information may be automatically generated based on medical information related to the heart stored in the ultrasound diagnosis apparatus 300 and information about the values of the parameters. Also, the diagnosis information may be input by the user.

The ultrasound diagnosis apparatus described herein may be implemented using hardware components, software components, and/or combination of the hardware components and the software components. For example, the apparatuses and the components described in the embodiments may be implemented using, for example, a processor, a controller, an arithmetic logic unit (ALU), a digital signal processor, a microcomputer, a field programmable array (FPA), a programmable logic unit (PLU), a microprocessor, or one or more general-purpose computers or specific-purpose computers such as any other device capable of responding to and executing instructions in a defined manner.

The processing device may run an operating system (OS) and one or more software applications that run on the OS. The processing device also may access, store, manipulate, process, and create data in response to execution of the software.

For convenience of comprehension, the description of a processing device is used as singular; however, one of ordinary skill in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a code, an instruction, or a combination of one or more thereof, for independently or collectively instructing or configuring the processing device to operate as desired.

Software and/or data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed manner. The software and data may be stored by one or more computer readable recording media.

The method according to the embodiments may be recorded in non-transitory computer-readable media including program instructions to implement various operations embodied by a computer. The non-transitory computer-readable media may also include, alone or in combination with the program instructions, data files, data structures, etc. The media and program instructions may be those specially designed and constructed for the purposes, or they may be of the kind well-known and available to those of skilled in the computer software arts.

Examples of non-transitory computer-readable media include magnetic media such as hard disks, floppy disks, and magnetic tape; optical media such as CD ROM disks and DVD; magneto-optical media such as floptical disks; and hardware devices that are specially to store and perform program instructions, such as read-only memory (ROM), random access memory (RAM), flash memory, etc.

Examples of the program instructions may include not only machine language codes but also high-level language codes which are executable by various computing means by using an interpreter.

The aforementioned hardware devices may be configured to operate as one or more software modules to carry out exemplary embodiments, and vice versa.

While the present disclosure has been described with reference to exemplary embodiments, one of ordinary skill in the art may practice various changes and modifications without departing from the spirit and scope of the present disclosure set forth throughout the annexed claim matters. For example, there may be attained a desired result according to the present disclosure even though the techniques are carried out through other methods and procedures different from the aforementioned, and/or even though the system, the structure, the units and the circuits are coupled in other manners different from the aforementioned, or substituted or replaced with other components or equivalents.

Therefore, it should be understood that other implementations, embodiments and equivalents involved in the claims may be construed as properly belonging to the territory of the present disclosure.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of operating an ultrasound diagnosis apparatus, the method comprising:
obtaining first Doppler data of a blood flow introduced into a right ventricle of an object and second Doppler data of a blood flow discharged from the right ventricle;
setting a landmark corresponding to a predetermined motion of a predetermined valve of the right ventricle in each of a first Doppler image generated based on the first Doppler data and a second Doppler image generated based on the second Doppler data;
synchronizing the first Doppler image and the second Doppler image to match times of the predetermined motion of the predetermined valve based on the set landmark; and
displaying the first Doppler image and the second Doppler image that are synchronized,
wherein the synchronizing of the first Doppler image and the second Doppler image comprises, synchronizing of the first Doppler image and the second Doppler image comprises, synchronizing, based on the set landmark, the first Doppler image and the second Doppler image, which are corrected such that heartbeat cycles of the object from the first Doppler data and the second Doppler data coincide with each other.

2. The method of claim 1, wherein the synchronizing of the first Doppler image and the second Doppler image comprises:
determining a first cycle of a heartbeat of the object based on the first Doppler data and a second cycle of the heartbeat of the object based on the second Doppler data;
when the first cycle and the second cycle are different from each other, correcting at least one of the first Doppler image and the second Doppler image to make the first cycle and the second cycle coincide with each other; and
synchronizing the first Doppler image and the second Doppler image having the coincided heartbeat cycle due to the correction, based on the landmark.

3. The method of claim 2, wherein the correcting of the at least one of the first and second Doppler images comprises:
correcting a scale in a time axis in a spectrum in the at least one of the first and second Doppler images so that the first cycle and the second cycle coincide with each other; and
correcting the Doppler data of the blood flow introduced into or discharged from the right ventricle in the spectrum of the at least one of the first and second Doppler images, according to the correction of the scale in the time axis.

4. The method of claim 2, wherein the correcting of the at least one of the first and second Doppler images comprises:
determining one of the first Doppler image and the second Doppler image as a reference Doppler image; and
correcting the other Doppler image not determined as the reference Doppler image based on the determined reference Doppler image, so that the first cycle and the second cycle coincide with each other.

5. The method of claim 1, wherein the predetermined motion of the right ventricle includes one of closing of a pulmonary valve (PV) of the right ventricle, opening of the PV of the right ventricle, closing of a tricuspid valve (TV) of the right ventricle, and opening of the TV of the right ventricle.

6. The method of claim 1, wherein the obtaining of the first Doppler data and the second Doppler data comprises:
obtaining an ultrasound image of the heart of the object;
obtaining the first Doppler data of the blood flow introduced into the right ventricle based on a sample volume gate set with respect to a TV of the right ventricle in the ultrasound image; and
obtaining the second Doppler data of the blood flow discharged from the right ventricle, based on a sample volume gate set with respect to a PV of the right ventricle in the ultrasound image.

7. The method of claim 1, further comprising:
obtaining a value of at least one parameter regarding a heart function, based on the first Doppler image and the second Doppler image that are synchronized; and
displaying the value of the at least one parameter.

8. The method of claim 7, wherein the at least one parameter comprises at least one of a closure time of a TV, an opening time of a PV, a myocardial performance index (MPI) regarding the heartbeat, an isovolumic relaxation time (IVRT) of the heart, and a isovolumetric contraction time (IVCT) of the heart.

9. The method of claim 7, wherein the displaying of the value of the at least one parameter comprises:
displaying the at least one parameter and the value of the at least one parameter on at least one of the synchronized first Doppler image and the synchronized second Doppler image; and
displaying diagnosis information of the heart, based on the value of the at least one parameter.

10. The method of claim 1, wherein the setting of the landmark comprises receiving an input of setting a landmark corresponding to the predetermined motion of the right ventricle in each of the first Doppler image and the second Doppler image through a user interface device for controlling operations of the ultrasound diagnosis apparatus.

11. An ultrasound diagnosis apparatus comprising:
a probe configured to transmit an ultrasound signal to a heart of an object, and to receive an echo signal reflected from the heart;
a processor configured to obtain first Doppler data of a blood flow introduced into a right ventricle and second Doppler data of a blood flow discharged from the right ventricle based on the echo signal, to set a landmark corresponding to a predetermined motion of a predetermined valve of the right ventricle in each of a first Doppler image generated based on the first Doppler data and a second Doppler image generated based on the second Doppler data, and to synchronize the first Doppler image and the second Doppler image to match times of the predetermined motion of the predetermined valve based on the set landmark; and
a display configured to display the first Doppler image and the second Doppler image that are synchronized with each other,
wherein the processor is further configured to synchronize, based on the set landmark, the first Doppler image and the second Doppler image, which are corrected such that heartbeat cycles of the object from the first Doppler data and the second Doppler data coincide with each other.

12. The ultrasound diagnosis apparatus of claim 11, wherein the processor is further configured to determine a first cycle of a heartbeat of the object based on the first Doppler data and a second cycle of the heartbeat of the object based on the second Doppler data, to correct at least one of the first Doppler image and the second Doppler image to make the first cycle and the second cycle coincide with each other when the first cycle and the second cycle are different from each other, and to synchronize the first Doppler image and the second Doppler image having the coincided heartbeat cycle due to the correction, based on the landmark.

13. The ultrasound diagnosis apparatus of claim 12, wherein the processor is further configured to correct a scale in a time axis in a spectrum in the at least one of the first and second Doppler images so that the first cycle and the second cycle coincide with each other, and to correct the Doppler data of the blood flow introduced into or discharged from the right ventricle in the spectrum of the at least one of the first and second Doppler images, according to the correction of the scale in the time axis.

14. The ultrasound diagnosis apparatus of claim 12, wherein the processor is further configured to determine one of the first Doppler image and the second Doppler image as a reference Doppler image, and to correct the other Doppler image not determined as the reference Doppler image based on the determined reference Doppler image, so that the first cycle and the second cycle coincide with each other.

15. The ultrasound diagnosis apparatus of claim 11, wherein the predetermined motion of the right ventricle includes one of closing of a pulmonary valve (PV) of the right ventricle, opening of the PV of the right ventricle, closing of a tricuspid valve (TV) of the right ventricle, and opening of the TV of the right ventricle.

16. The ultrasound diagnosis apparatus of claim 11, wherein the processor is further configured to obtain an ultrasound image of the heart of the object based on the echo signal, to obtain the first Doppler data of the blood flow introduced into the right ventricle based on a sample volume gate set with respect to a TV of the right ventricle in the ultrasound image, and to obtain the second Doppler data of the blood flow discharged from the right ventricle, based on a sample volume gate set with respect to a PV of the right ventricle in the ultrasound image.

17. The ultrasound diagnosis apparatus of claim 11, wherein the processor is further configured to obtain a value of at least one parameter regarding a heart function, based on the first Doppler image and the second Doppler image that are synchronized, and the display is further configured to display the value of the at least one parameter.

18. The ultrasound diagnosis apparatus of claim 17, wherein the at least one parameter comprises at least one of a closure time of a TV, an opening time of a PV, a myocardial performance index (MPI) regarding the heartbeat, an isovolumic relaxation time (IVRT) of the heart, and a isovolumetric contraction time (IVCT) of the heart.

19. The ultrasound diagnosis apparatus of claim 17, wherein the display is further configured to display the at least one parameter and the value of the at least one parameter on at least one of the synchronized first Doppler image and the synchronized second Doppler image, and to display diagnosis information of the heart, based on the value of the at least one parameter.

20. The ultrasound diagnosis apparatus of claim 11, further comprising a user interface device configured to control operations of the ultrasound diagnosis apparatus, wherein the user interface device is configured to receive an input for setting a landmark corresponding to the predetermined motion of the right ventricle in the first Doppler image and the second Doppler image.

21. A computer-readable recording medium having embodied thereon a program for executing a method of operating an ultrasound diagnosis apparatus, wherein the method comprises:
obtaining first Doppler data of a blood flow introduced into a right ventricle of an object and second Doppler data of a blood flow discharged from the right ventricle;
setting a landmark corresponding to a predetermined motion of a predetermined valve of the right ventricle in each of a first Doppler image generated based on the first Doppler data and a second Doppler image generated based on the second Doppler data;
synchronizing the first Doppler image and the second Doppler image to match times of the predetermined motion of the predetermined valve based on the set landmark; and
displaying the first Doppler image and the second Doppler image that are synchronized,
wherein the synchronizing of the first Doppler image and the second Doppler image comprises, synchronizing, based on the set landmark, the first Doppler image and the second Doppler image, which are corrected such that heartbeat cycles of the object from the first Doppler data and the second Doppler data coincide with each other.

* * * * *

UNITED STATES PATENT AND TRADEMARK OFFICE
CERTIFICATE OF CORRECTION

PATENT NO. : 10,966,686 B2
APPLICATION NO. : 15/870475
DATED : April 6, 2021
INVENTOR(S) : Park et al.

It is certified that error appears in the above-identified patent and that said Letters Patent is hereby corrected as shown below:

In the Claims

Column 21, Lines 10-12:
Delete "synchronizing of the first Doppler image and the second Doppler image comprises,"

Signed and Sealed this
Nineteenth Day of April, 2022

Katherine Kelly Vidal
*Director of the United States Patent and Trademark Office*